US011331359B2

(12) United States Patent
Jia et al.

(10) Patent No.: US 11,331,359 B2
(45) Date of Patent: May 17, 2022

(54) COMPOSITIONS, METHODS, AND MEDICAL COMPOSITIONS FOR TREATMENT OF AND MAINTAINING THE HEALTH OF THE LIVER

(71) Applicant: Unigen, Inc., Seattle, WA (US)

(72) Inventors: Qi Jia, Olympia, WA (US); Mesfin Yimam, Tacoma, WA (US); Ping Jiao, Newcastle, WA (US); Mei Feng Hong, Seattle, WA (US); Breanna Moore, Seattle, WA (US)

(73) Assignee: Unigen, Inc., Tacoma, WA (US)

( * ) Notice: Subject to any disclaimer, the term of this patent is extended or adjusted under 35 U.S.C. 154(b) by 471 days.

(21) Appl. No.: 15/208,075

(22) Filed: Jul. 12, 2016

(65) Prior Publication Data
US 2017/0014461 A1 Jan. 19, 2017

Related U.S. Application Data

(60) Provisional application No. 62/192,711, filed on Jul. 15, 2015.

(51) Int. Cl.
*A61K 36/282* (2006.01)
*A61K 36/886* (2006.01)
*A61K 36/79* (2006.01)
*A61K 45/06* (2006.01)
*A61K 31/7048* (2006.01)

(52) U.S. Cl.
CPC ........ *A61K 36/282* (2013.01); *A61K 31/7048* (2013.01); *A61K 36/79* (2013.01); *A61K 36/886* (2013.01); *A61K 45/06* (2013.01); *A61K 2236/33* (2013.01); *A61K 2236/333* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| | | | |
|---|---|---|---|
| 2002/0102237 A1* | 8/2002 | Hammerly | A61K 36/28 424/85.5 |
| 2010/0092584 A1* | 4/2010 | Lee | A61K 36/07 424/740 |
| 2015/0050371 A1 | 2/2015 | Gehling et al. | |

FOREIGN PATENT DOCUMENTS

| | | | |
|---|---|---|---|
| CN | 103110887 A | * | 5/2013 |
| EP | 2502629 | | 9/2012 |
| GE | P20012394 | | 5/1998 |
| WO | WO 95/23604 A1 | * | 9/1995 |

OTHER PUBLICATIONS

He (Experimental and Therapeutic Medicine (2012), vol. 4, pp. 645-648).*
Ajith TA, Hema U, Aswathy MS. Zingiber officinale Roscoe prevents acetaminophen-induced acute hepatotoxicity by enhancing hepatic antioxidant status. Food Chem. Toxicol. 2007; 45:2267-2272.
Albano E., Lott A.K., Slater T.F., Stier A., Symons M.C.R., and Tomasi A. (1982) Spin trapping studies on the free radical products formed by metabolic activation of carbon tetrachloride in rat liver microsomal fractions, isolated hepatocytes and in vivo. Biochem. J. 204:593-603.
Amat N, Upur H, Blazeković B. In vivo hepatoprotective activity of the aqueous extract of Artemisia absinthium L. against chemically and immunologically induced liver injuries in mice. J Ethnopharmacol. 2010; 131(2):478-84.
An RB, Sohn DH, Kim YC. Hepatoprotective compounds of the roots of Cudrania tricuspidata on tacrine-induced cytotoxicity in Hep G2 cells. Biol Pharm Bull. 2006; 29(4):838-40.
Bajt ML, Cover C, Lemasters JJ, Jaeschke H. Nuclear translocation of endonuclease G and apoptosisinducing factor during acetaminophen-induced liver cell injury. Toxicol. Sci. 2006; 94:217-225.
Bajt ML, Farhood A, Lemasters JJ, Jaeschke H. Mitochondrial bax translocation accelerates DNA fragmentation and cell necrosis in a murine model of acetaminophen hepatotoxicity. J. Pharmacol. Exp. Ther. 2008; 324:8-14.
Bajt ML, Ramachandran A, Yan HM, Lebofsky M, Farhood A, Lemasters JJ, Jaeschke H. Apoptosis-Inducing factor modulates mitochondrial oxidant stress in acetaminophen hepatotoxicity. Toxicol. Sci. 2011; 122:598-605.
Choi JH, Kim DW, Yun N, Choi JS, Islam MN, Kim YS, et al. Protective effects of hyperoside against carbon tetrachloride-induced liver damage in mice. J Nat Prod. 2011; 74:1055-60.
Choi MK, Han JM, Kim HG, Lee JS, Lee JS, Wang JH, Son SW, Park HJ, Son CG. Aqueous extract of Artemisia capillaris exerts hepatoprotective action in alcohol-pyrazole-fed rat model. J Ethnopharmacol. 2013; 147(3):662-70.
Koo HN, Hong SH, Jeong HJ, Lee EH, Kim NG, Choi SD, et al. Inhibitory effect of Artemisia Capillaris on ethanol-induced cytokines (TNF-α, IL-1α) secretion in Hep G2 cells. Immunopharmacol Immunotoxicol. 2002; 24:441-53.
Hogade MG, Patil ks, Wadkar GH, Mathapati SS, Dhumal P. Hepatoprotective activity of Morus alba (Linn.) leaves extract against carbon tetrachloride induced hepatotoxicity in rats. African Journal of Pharmacy and Pharmacology 2010; vol. 4(10), pp. 731-734.

(Continued)

Primary Examiner — Susan Hoffman
(74) Attorney, Agent, or Firm — Sandra Poteat Thompson; Finlayson Toffer Roosevelt & Lilly LLP

(57) ABSTRACT

Compositions and methods for treatment of and maintaining the health of the liver are disclosed that include a mixture of plant extracts, wherein the plant extracts comprise at least one *Artemisia* extract, at least one *Aloe* gel powder, and at least one *Schizandra* extract. Compositions and methods for treatment of and maintaining the health of the liver are disclosed that include a mixture of plant extracts, wherein the plant extracts comprise at least one *Artemisia* extract enriched for at least one polymer or biopolymer, at least one *Aloe* gel powder enriched for at least one chromone, and at least one *Schizandra* extract enriched for at least one lignan and organic acid.

17 Claims, 1 Drawing Sheet

(56) References Cited

OTHER PUBLICATIONS

Hong SH, Seo SH, Lee JH, Choi BT. The aqueous extract from Artemisia capillaris Thunb. Inhibits lipopolysaccharide-induced inflammatory response through preventing NF-kappaB activation in human hepatoma cell line and rat liver. Int J Mol Med. 2004; 13(5):717-20.

Hong JH, Lee IS. Cytoprotective effect of Artemisia Capillaris fractions on oxidative stress-induced apoptosis in V79 cells. Biofactors. 2009; 35:380-8.

Jaeschke H. Glutathione disulfide formation and oxidant stress during acetaminophen-induced hepatotoxicity in mice in vivo: the protective effect of allopurinol. J. Pharmacol. Exp. Ther. 1990; 255:935-941.

Chamulitrat W., Jordan S.J., and Mason R.P. (1994) Nitric oxide production during endotoxic shock in carbon tetrachloride-treated rats. Mol. Pharmacol. 46:391-397.

Chamulitrat W., Blazka M.E., Jordan S.J., Luster M.I., and Mason R.P. (1995) Tumor necrosis factor-alpha and nitric oxide production in endotoxin-primed rats administered carbon tetrachloride. Life Sci. 57:2273-2280.

Chu CY, Tseng TH, Hwang JM, Chou FP, Wang CJ. Protective effects of capillarisin on tert-butylhydroperoxide-induced oxidative damage in rat primary hepatocytes. Arch Toxicol. 1999; 73:263-8.

Sung-Hwan Kim et al: "Evaluation of the toxicological properties and hepatoprotective effects of PAI-N002, a mixture of herbal extracts in rats", Molecular and Cellular Toxicology, vol. 6, No. 3, Sep. 1, 2010, pp. 239-246.

Duangpom Werawatganon et al, "Aloe vera attenuated liver injury in mice with acetaminophen-induced hepatitis", BMC Complementary and Alternative Medicine, vol. 53, No. 1, Dec. 1, 2014, p. 392.

Cha JD, Moon SE, Kim HY, Lee JC, Lee KY. The essential oil isolated from Artemisia Capillaris prevents LPS-induced production of NO and PGE(2) by inhibiting MAPK-mediated pathways in RAW 264.7 macrophages. Immunol Invest. 2009; 38:483-97.

Singab AN, Ayoub NA, Ali EN, Mostafa NM. Antioxidant and hepatoprotective activities of Egyptian moraceous plants against carbon tetrachloride-induced oxidative stress and liver damage in rats. Pharm Biol. 2010; 48(11):1255-64.

Wan Y, Wu YL, Lian LH, Nan JX. Protective effect of Ornithogalum saundersiae Ait (Liliaceae) against acetaminophen-induced acute liver injury via CYP2E1 and HIF-1α. Chin. J. Nat. Med. 2012; 10:177-184.

Kwon OS, Choi JS, Islam MN, Kim YS, Kim HP. Inhibition of 5-lipoxygenase and skin inflammation by the aerial parts of Artemisia Capillaris and its constituents. Arch Pharm Res. 2011; 34:1561-9.

Mitchell JR, Jollow DJ, Potter WZ, Davis DC, Gillette JR, Brodie BB. Acetaminophen-induced hepatic necrosis. I. Role of drug metabolism. J. Pharmacol. Exp. Ther. 1973; 187:185-194.

Park KM, Li Y, Kim B, Zhang H, Hwangbo K, Piao DG, Chi MJ, Woo MH, Choi JS, Lee JH, Moon DC, Chang HW, Kim JR, Son JK. High-performance liquid chromatographic analysis for quantitation of marker compounds of Artemisia capillaris Thunb. Arch Pharm Res. 2012; 35(12):2153-2162.

Qiu Y, Benet LZ, Burlingame AL. identification of hepatic protein targets of the reactive metabolites of the non-hepatotoxic regioisomer of acetaminophen, 3'-hydroxyacetanilide, in the mouse in vivo using two-dimensional gel electrophoresis and mass spectrometry. Adv. Exp. Med. Biol. 2001; 500:663-673.

Jaeschke H, McGill MR, Ramachandran A. Oxidant stress, mitochondria, and cell death mechanisms in drug-induced liver injury: lessons learned from acetaminophen hepatotoxicity. Drug Metab. Rev. 2012a; 44:88-106.

Jollow DJ, Mitchell JR, Potter WZ, Davis DC, Gillette JR, Brodie BB. Acetaminophen-induced hepatic necrosis. II. Role of covalent binding in vivo. J. Pharmacol. Exp. Ther. 1973; 187:195-202.

Kim SW, Kim HW, Woo MH, Lee JH, Choi JS, Min BS. Quantitative determination of bioactive compounds in some Artemisia capillaris by high-performance liquid chromatography. Nat Prod Sci. 2010; 16(4):233-238.

Colby, SR. Calculating Synergistic and Antagonistic Responses of Herbicide combinations. Weeds, vol. 15, No. 1 (Jan. 1967), pp. 20-22.

Cover C, Mansouri A, Knight TR, Bajt ML, Lemasters JJ, Pessayre D, Jaeschke H. Peroxynitriteinduced mitochondrial and endonuclease-mediated nuclear DNA damage in acetaminophen hepatotoxicity. J. Pharmacol. Exp. Ther. 2005; 315:879-887.

Czaja M.J., Xu J., and Alt E. (1995) Prevention of carbon tetrachloride-induced rat liver injury by soluble tumor necrosis factor receptor. Gastroenterology 108:1849-1854.

Davern TJ 2nd, James LP, Hinson JA, Polson J, Larson AM, Fontana RJ, Lalani E, Munoz S, Shakil AO, Lee WM, Acute Liver Failure Study Group. Measurement of serum acetaminophen-protein adducts in patients with acute liver failure. Gastroenterology. 2006; 130:687-694.

Feng G, Wang X, You C, Cheng X, Han Z, Zong L, Zhou C, Zhang M. Antiproliferative potential of Artemisia capillaris polysaccharide against human nasopharyngeal carcinoma cells. Carbohydr Polym. 2013; 15; 92(2):1040-5.

Han KH, Jeon YJ, Athukorala Y, Choi KD, Kim CJ, Cho JK, et al. A water extract of Artemisia Capillaris prevents 2,2'-azobis(2-amidinopropane) dihydrochloride-induced liver damage in rats. J Med Food. 2006; 9:342-7.

Hanawa N, Shinohara M, Saberi B, Gaarde WA, Han D, Kaplowitz N. Role of JNK translocation to mitochondria leading to inhibition of mitochondria bioenergetics in acetaminophen-induced liver injury. J. Biol. Chem. 2008; 283:13565-13577.

He CS, Yue HY, Xu J, Xue F, Liu J, Li YY, Jing HE. Protective effects of capillary artemisia polysaccharide on oxidative injury to the liver in rats with obstructive jaundice. Exp Ther Med. 2012; 4(4):645-648.

Hu YQ, Tan RX, Chu MY, Zhou J. Apoptosis in human hepatoma cell line SMMC-7721 induced by water-soluble macromolecular components of Artemisia capillaris Thunberg. Jpn J Cancer Res. 2000; 91(1):113-7.

Hung HY, SC. Recent Studies and Progression of Yin Chen Hao (茵陳蒿 Yīn Chén Hāo), a Long-term Used Traditional Chinese Medicine. J Tradit Complement Med. 2013; 3(1): 2-6.

Jaeschke H, Williams CD, McGill MR, Xie Y, Ramachandran A. Models of drug-induced liver injury for evaluation of phytotherapeutics and other natural products. Food Chem Toxicol. May 2013;55:279-89.

James LP, Letzig L, Simpson PM, Capparelli E, Roberts DW, Hinson JA, Davern TJ, Lee WM. Pharmacokinetics of acetaminophen-protein adducts in adults with acetaminophen overdose and acute liver failure. Drug Metab. Dispos. 2009; 37:1779-1784.

Jung HA, Park JJ, Islam MN, Jin SE, Min BS, Lee JH, et al. Inhibitory activity of coumarins from Artemisia Capillaris against advanced glycation end product formation. Arch Pharm Res. 2012; 35:1021-35.

Kim DW, Cho HI, Kim KM, Kim SJ, Choi JS, Kim YS, et al. Isorhamnetin-3-O-galactoside protects against CCl4-Induced hepatic injury in mice. Biomol Ther. 2012; 20:406-12.

Kim EK, Kwon KB, Han MJ, Song MY, Lee JH, Lv N, et al. Inhibitory effect of Artemisia Capillaris extract on cytokine-induced nitric oxide formation and cytotoxicity of RINm5F cells. Int J Mol Med. 2007; 19:535-40.

Kon K, Kim JS, Jaeschke H, Lemasters JJ. Mitochondrial permeability transition in acetaminopheninduced necrosis and apoptosis of cultured mouse hepatocytes. Hepatology. 2004; 40:1170-1179.

Larson AM. Acetaminophen hepatotoxicity. Clin. Liver Dis. 2007; 11:525-548.

Lee HI, Seo KO, Yun KW, Kim MJ, Lee MK. Comparative study of the hepatoprotective efficacy of Artemisia iwayomogi and Artemisia capillaris on ethanol-administered mice. J Food Sci. 2011; 76(9):T207-11.

Loguidice A, Boelsterli UA. Acetaminophen overdose-induced liver injury in mice is mediated by peroxynitrite independently of the cyclophilin D-regulated permeability transition. Hepatology. 2011; 54:969-978.

(56) References Cited

OTHER PUBLICATIONS

Luckey S.W. and Petersen D.R. (2001) Activation of Kupffer cells during the course of carbon tetrachloride-induced liver injury and fibrosis in rats Exp. Mol. Pathol. 71:226-240.

Masubuchi Y, Suda C, Horie T. Involvement of mitochondrial permeability transition in acetaminophen-induced liver injury in mice. J. Hepatol. 2005; 42:110-116.

McGill MR, Sharpe MR, Williams CD, Taha M, Curry SC, Jaeschke H. The mechanism underlying acetaminophen-induced hepatotoxicity in humans and mice involves mitochondrial damage and nuclear DNA fragmentation. J. Clin. Invest. 2012a; 122:1574-1583.

McGill MR, Williams CD, Xie Y, Ramachandran A, Jaeschke H. Acetaminophen-induced liver injury in rats and mice: Comparison of protein adducts, mitochondrial dysfunction, and oxidative stress in the mechanism of toxicity. Toxicol. Appl. Pharmacol. 2012b; 264:387-394.

Nakagawa H, Maeda S, Hikiba Y, Ohmae T, Shibata W, Yanai A, Sakamoto K, Ogura K, Noguchi T, Karin M, Ichijo H, Omata M. Deletion of apoptosis signal-regulating kinase 1 attenuates acetaminophen-induced liver injury by inhibiting c-Jun N-terminal kinase activation. Gastroenterology. 2008; 135:1311-21.

Panossian A, Wikman G. Pharmacology of Schisandra chinensis Bail.: an overview of Russian research and uses in medicine. J Ethnopharmacol. 2008; 118(2):183-212.

Poyer J.L., McCay P.B., Lai E.K., Janzen E.G., and Davis E.R. (1980) Confirmation of assignment of trichloromethyl radical spin adduct detected by spin trapping during 13C carbon tetrachloride metabolism in vitro and in vivo. Biochem. Biophys. Res. Commun. 94:1154-1160.

Ramachandran A, Lebofsky M, Baines CP, Lemasters JJ, Jaeschke H. Cyclophilin D deficiency protects against acetaminophen-induced oxidant stress and liver injury. Free Radic. Res. 2011a; 45:156-164.

Reynolds E.S. (1963) Liver parenchymal cell injury. I. Initial alterations of the cell following poisoning with carbon tetrachloride. J. Cell Biol. 19:139-157.

Saito C, Lemasters JJ, Jaeschke H. c-Jun N-terminal kinase modulates oxidant stress and peroxynitrite formation independent of inducible nitric oxide synthase in acetaminophen hepatotoxicity. Toxicol. Appl. Pharmacol. 2010a; 246:8-17.

Tien YC, Liao JC, Chiu CS, Huang TH, Huang CY, Chang WT, et al. Esculetin ameliorates carbon tetrachloride-mediated hepatic apoptosis in rats. Int J Mol Sci. 2011; 12:4053-67.

Tirmenstein MA, Nelson SD. Subcellular binding and effects on calcium homeostasis produced by acetaminophen and a nonhepatotoxic regioisomer, 3'-hydroxyacetanilide, in mouse liver. J. Biol.Chem. 1989; 264:9814-9819.

Wang JH, Choi MK, Shin JW, Hwang SY, Son CG. Antifibrotic effects of Artemisia capillaris and Artemisia iwayomogi in a carbon tetrachloride-induced chronic hepatic fibrosis animal model. J Ethnopharmacol. 2012;140(1):179-85.

Weddle CC, Hornbrook KR, McCay PB. Lipid peroxidation and alteration of membrane lipids in isolated hepatocytes exposed to carbon tetrachloride. J. Biol. Chem. 1976; 251:4973-4978.

Yang CC, Fang JY, Hong TL, Wang TC, Zhou YE, Lin TC. Potential antioxidant properties and hepatoprotective effects of an aqueous extract formula derived from three Chinese medicinal herbs against CCl(4)-induced liver injury in rats. Int Immunopharmacol. 2013; 15(1):106-13.

Zaher H, Buters JT, Ward JM, Bruno MK, Lucas AM, Stern ST, Cohen SD, Gonzalez FJ. Protection against acetaminophen toxicity in CYP1A2 and CYP2E1 double-null mice. Toxicol. Appl. Pharmacol. 1998; 152:193-199.

Zhao Y, Geng CA, Ma YB, Huang XY, Chen H, Cao TW, He K, Wang H, Zhang XM, Chen JJ. UFLC/MS-IT-TOF guided isolation of anti-HBV active chlorogenic acid analogues from Artemisia capillaris as a traditional Chinese herb for the treatment of hepatitis. J Ethnopharmacol. 2014; 156:147-54.

* cited by examiner

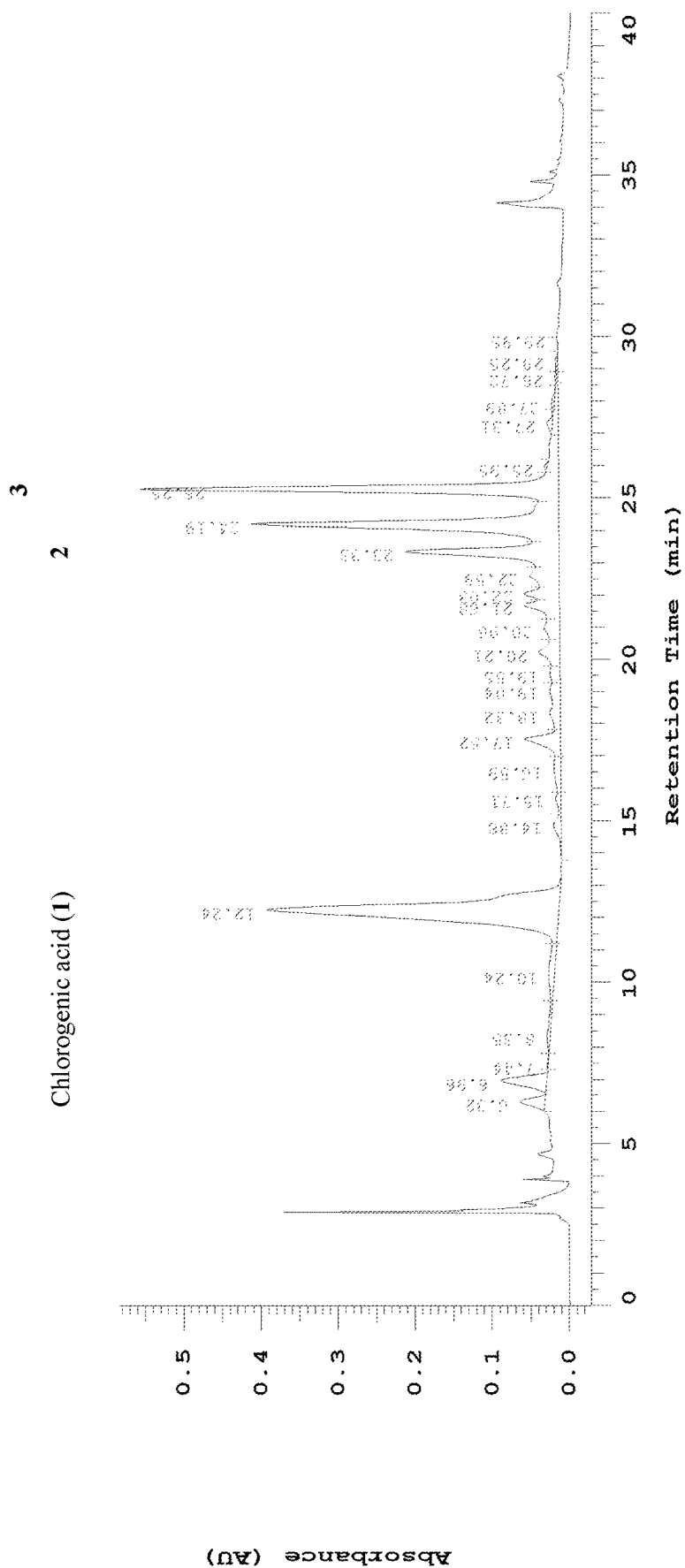
Figure 1. HPLC chromatogram of *Artemisia capillaris* 70% ethanol extract

COMPOSITIONS, METHODS, AND MEDICAL COMPOSITIONS FOR TREATMENT OF AND MAINTAINING THE HEALTH OF THE LIVER

This United States Utility Application claims priority to U.S. Provisional Patent Application Ser. No. 62/192,711 filed on Jul. 15, 2015 and entitled "Compositions and Methods for Liver Health", which is commonly-owned and incorporated herein in its entirety by reference.

FIELD OF THE SUBJECT MATTER

The field of the subject matter is compounds and compositions useful for liver health management, including stereoisomers, pharmaceutically or nutraceutically acceptable salts, tautomers, glycosides and prodrugs of the disclosed compounds, compositions and related methods of improving and maintaining liver health.

BACKGROUND

The liver is a vital organ that plays a pivotal role in metabolism and detoxification of various endogenous and exogenous harmful substances. It is believed that more than 500 chemical reactions take place in the liver. Various xenobiotics or foreign chemical substances are known to cause hepatotoxicity, among which acetaminophen (n-acetyl-p-aminophenol or APAP) and carbon tetrachloride ($CCl_4$) are generally utilized to develop an animal model that mimics the human type of liver toxicity with similar mechanisms of actions. Ranges of biomarkers from serum or liver homogenates have been used to review and/or analyze the health status of the liver where a shift away from the normal range is considered an indication of insult to the organ. Among these biomarkers, the most frequently used are: ALT (alanine aminotransferase), AST (aspartate aminotransferase), MDA (malondialdehyde), GSH (glutathione), SOD (superoxide dismutase), c-Jun N-terminal kinase (JNK), GSH-Px (glutathione peroxidase), CAT (catalase), and TNF-alpha (tumor necrosis factor-alpha). Liver panels such as AST, ALT, total bilirubin, conjugated and unconjugated bilirubin, bile acid, total protein, albumin, globulin, and alkaline phosphatase have been used as a standard screen method for liver health. While ALT and AST are recognized as non-specific to liver injury, ALT has shown relative specificity to the liver. For example, AST has an origin ratio of liver (9000:1) vs muscle (5200:1); in comparison ALT has an origin ratio of liver (7600:1) vs muscle (750:1). The half-life of total AST and ALT are 17±5 hours and 47±10 hours, respectively. ALT is stable for 3 days at room temperature, 3 weeks in a refrigerator, 24 hours in whole blood; however, ALT deteriorates rapidly with repeated freezing and thawing. Serum ALT was used for efficacy screening of plant extracts in our studies.

APAP is a very safe and effective analgesic and antipyretic drug at therapeutic dosage. It is the most frequent cause of acute live failure in the United States. APAP-induced liver toxicity is clinically relevant, well studied, can be rapidly induced in vivo with a single dose, and has become a conventional model in assessing the potential hepatoprotective effects of phytotherapeutics.

APAP-induced cell death is not caused by a single tragic event shutting down vital function of cells instead it induces a series of events beginning with the reactive metabolite formation and initiation of mitochondrial dysfunction, which is amplified through the JNK pathway, ultimately leading to non-functional mitochondria and massive DNA degradation leading to cell necrosis.

APAP toxicity takes place in very intricate pathways of mechanisms of actions. As previously established, the intracellular signaling mechanisms of APAP-induced cell death is initiated by the metabolism of a small fraction of the administered dose by P450 enzymes, mainly Cyp 2e1 and 1a2 (Zaher et al., 1998), to n-acetyl-p-benzoquinone imine (NAPQI). Under normal conditions, this highly reactive metabolite will be detoxified by GSH resulting in extensive hepatic GSH depletion (Mitchell et al., 197), which becomes critical at the time of overdose. Concurrently, an increasing amount of NAPQI reacts with protein sulfhydryl groups, causing the covalent adduction of cellular proteins (Jollow et al., 1973). Interestingly, studies have shown that the total protein binding in the cell is not as important as adducts in mitochondria (Tirmenstein and Nelson, 1989; Qiu et al., 2001). Mitochondrial protein binding triggers a mitochondrial oxidant stress (Jaeschke, 1990), which causes activation of apoptosis signal-regulating kinase 1 (Nakagawa et al., 2008) and c-Jun N-terminal kinase (JNK) (Hanawa et al., 2008) and the amplification of the mitochondrial oxidant stress and peroxynitrite formation by mitochondrial JNK translocation (Saito et al., 2010a). The extensive oxidant stress finally triggers the opening of the membrane permeability transition (MPT) pore in the mitochondria with collapse of the membrane potential (Kon et al., 2004; Masubuchi et al., 2005; Ramachandran et al., 2011a; Loguidice and Boelsterli, 2011) followed by the release of intermembrane proteins such as endonuclease G and apoptosis inducing factor (AIF) from mitochondria (Kon et al., 2004; Bajt et al., 2008). Both endonuclease G and AIF translocate to the nucleus and cause DNA fragmentation (Cover et al., 2005; Bajt et al., 2006, 2011) and ultimately cell death occurs. The collapse of the mitochondrial membrane potential with ATP depletion and the nuclear degradation are key events leading to cellular necrosis. Hence, there are multiple interference points where these mechanisms can be intercepted when designing therapeutic intervention for liver protection.

Knowing chronology of the pathologic process of the model provides a guideline for therapeutic intervention. While oxidative stress and sterile inflammations play a significant role in APAP toxicity, pathophysiology of the model is characterized by a series of events, including metabolic activation between 0 and 2 h, depletion of GSH within the first 30 minutes, intracellular mechanisms of cell death between 2 and 12 h, an inflammatory response at time frame of 6-24 h, and regeneration in the timeframe of 24-72 h after APAP toxicity (Jaeschke et al., 2012a).

As mentioned, APAP overdose can cause severe liver toxicity in humans characterized by protein adduct formation (Davern et al., 2006; James et al., 2009), mitochondrial damage and nuclear DNA fragmentation (McGill et al., 2012a) that leads to cell death. Therefore, it is desirable to utilize animal models that could share similar pathophysiology features when testing plant extracts for liver protection. Thus, for in vivo experiments, the mouse is the preferred model, as the damage most closely resembles the human pathophysiology in both mechanism and dose-dependency. In fact, some suggest that the primary significant difference in APAP hepatotoxicity between mice and humans is the more delayed toxicity in humans which exhibits ALT peak at 24-48 h after exposure compared to mice when ALT peaks at 6-12 h (Larson, 2007). This difference may in part be explained because of differences in absorption between the two species. In contrast, the rat, although popular for natural product testing, is a poor model as most rat strains are largely insensitive to APAP toxicity (Mitchell et al., 1973; McGill et al., 2012b). Even at high dose of ≥1 g/kg, APAP mostly does not cause relevant liver injury (Jaeschke et al., 2013). And while GSH depletion and protein adducts can be measured, the lower adducts in rat liver mitochondria compared to mice appear to be insufficient to initiate enough mitochondrial dysfunction and subsequent amplification events to lead to necrotic cell death (McGill et al., 2012b). These fundamental differences between the two species have been reflected during evaluation of phytotherapeutics. For example, in a rat study, an APAP dose of 3 g/kg resulted in an increase of plasma ALT levels of about 3-fold compared to baseline and the phytotherapeutic attenuated this modest liver injury by 33% (Ajith et al., 2007). Any histological changes in this rat model were minimal and difficult to detect. On the other hand, in a mouse study, ALT increases were >60-fold of baseline after a 300 mg/kg APAP dose and the reduction by the phytotherapeutic was 75% (Wan et al., 2012). Histological changes caused by APAP toxicity and the protective effect of the drug were readily observed.

$CCl_4$, a halogenated alkane industrial chemical with restricted usage, is a well-known hepatotoxin that is widely used to induce acute toxic liver injury in a large range of laboratory animals. Humans have been exposed to $CCl_4$, in occupational surroundings and from environmental contamination, such as contaminated drinking water. Nevertheless, the chemical continues to provide an important service today as a model compound to elucidate the mechanisms of action of hepatotoxic effects such as fatty degeneration, fibrosis, hepatocellular death, and carcinogenicity (Slater 1981; Renner H. 1985; Reynolds 1963). It is considered as one of the classic chemically-induced liver toxicity animal models primarily associated with the formation of free radicals and lipid peroxidation.

Like APAP, $CCl_4$ toxicity is initiated by cytochrome P450s primarily of (CYP) 2E1, CYP2B1 or CYP2B2 (Nelson and Harrison, 1987), to yield reactive metabolic products trichloromethyl free radicals ($CCl_3$—), which can initiate lipid peroxidation and ultimately results in the overproduction of reactive oxygen species (ROS) and hepatocyte injuries (Poyer et al., 1980; Albano et al., 1982). In the process, these radicals can bind to cellular molecules (nucleic acid, protein, and lipid), impairing crucial cellular processes, such as lipid metabolism, with the potential outcome of fatty degeneration (steatosis) and direct damage to these macromolecules (Weddle et al., 1976). These radicals can also react with oxygen to form the trichloromethylperoxy radical $CCl_3OO$—, a highly reactive species. Once generated, it initiates the chain reaction of lipid peroxidation, which attacks and destroys polyunsaturated fatty acids, in particular those associated with phospholipids. This affects the permeability of mitochondrial, endoplasmic reticulum, and plasma membranes, resulting in the loss of cellular calcium sequestration and homeostasis, which can contribute heavily to subsequent cell damage. In this respect, antioxidants and radical scavengers have been used to study the mechanism of $CCl_4$ toxicity as well as to protect liver cells from $CCl_4$-induced damage by breaking the chain reaction of lipid peroxidation (Cheeseman et al., 1987). At the molecular level, $CCl_4$ activates TNF-α (Czaja et al., 1995), nitric oxide (NO) (Chamulitrat et al., 1994, 1995), and transforming growth factors (TGF) (Luckey et al., 2001) in the cell, processes that appear to direct the cell primarily toward destruction or fibrosis. These suggest that plant extracts with anti-inflammatory activity could have a potential application in liver protection. While acute administration of a large dose of $CCl_4$ causes severe necrosis, chronic administration of lower doses is frequently used to induce hepatic fibrosis.

Oxidative stress is an imbalance between the production of free radicals and the inherent capacity of the body to counteract or neutralize their harmful effects through interaction with various reducing and sequestering endogenous antioxidant defense networks. When there is a lack of an appropriate adaptation by the body antioxidant defense system, reactive oxygen species accumulation will lead to the activation of stress-sensitive intracellular signaling pathways that, in turn, promote cellular damage leading to necrosis. While damage of oxidative stress affects the whole body as a system, the impact becomes more detrimental when it involves vital organs, such as the liver, where primary detoxification takes place to remove and metabolize harmful toxins such as alcohol. As a result, the liver is susceptible to alcohol-induced injury as both alcohol and its primary metabolite acetaldehyde produce reactive oxygen species (ROS) and hydroxyl radicals (OH), altering hepatic antioxidant defense system. The most common pathological conditions such as fatty liver, hepatitis, fibrosis, and cirrhosis are observed in alcohol-linked liver disorders as a result of repeated exposure of alcohol. These outcomes in conjunction with cellular lipids, proteins, and DNA oxidation has been demonstrated in multiple experimental animals (Wu and Cederbaum, 2003). Here we used the most frequently used animal model with practical clinical implications, such as APAP, and confirmed findings with the classic $CCl_4$-induced hepatotoxicity model. Regardless of the chemical agents used to induce the hepatotoxicity, both the APAP and $CCl_4$ models share the critical step in oxidative stress induced by reactive oxygen species generated by excess intermediate metabolites leading to protein oxidation, lipid peroxidation, and DNA damage.

To this end, it would be desirable to develop, produce and utilize a composition, medicinal composition and related methods that are designed to treat and maintain the health of the liver. Ideal compounds, medicinal compositions and compositions would be sufficient to effect treatment, including any one or more of: (1) treating or preventing damage of liver cells in a mammal; (2) promoting liver health; (3) preserve detoxification and anti-oxidation liver enzymes in a mammal; (4) increasing liver detoxification capacity in a mammal; (5) treating or preventing liver diseases in a mammal; (6) modifying inflammation of a liver in a mammal; and (7) improving liver renewal function. Ideal compounds and compositions can be derived from or comprise at least one plant extract, wherein the plant extract may or may not be enriched. As part of this development, it would be ideal to utilize frequently and acceptable models to test contemplated compounds and compositions. It would also be desirable to reliably design a therapeutic intervention for liver health by intercepting points in the mechanisms of liver degradation and studying those results.

SUMMARY OF THE SUBJECT MATTER

Compositions and methods for treatment of and maintaining the health of the liver are disclosed that include a mixture of plant extracts, wherein the plant extracts comprise at least one *Artemisia* extract, at least one *Aloe* gel powder, and at least one *Schizandra* extract.

Compositions and methods for treatment of and maintaining the health of the liver are disclosed that include a mixture of plant extracts, wherein the plant extracts comprise at least one *Artemisia* extract enriched for at least one polymer or biopolymer, at least one *Aloe* gel powder enriched for at least one chromone, and at least one *Schizandra* extract enriched for at least one lignan and organic acid.

Medical compositions and methods for maintaining liver function, minimizing liver cell damage, promoting healthy liver, protecting liver antioxidation integrity, neutralizing toxins, diminishing the action of free radicals that affecting liver health, scavenging reactive oxygen species, reducing oxidative stress, preventing the formation of toxic metabolisms, improving liver detoxification capacity and/or function, liver cleansing, restoring liver structure, liver protecting liver cells from toxins, helping liver's blood flow and circulation, supporting liver function, fortifying and soothing lever, calming and tonifying liver, alleviating liver pain, purging harmful chemicals and organisms, supporting liver's metabolic process, alleviating liver discomfort, alleviating fatty liver, improving liver detoxification capacity, lowering liver enzymes, providing natural oxidants, increasing SOD, increasing GSH, reducing liver cell peroxidation, reducing fatty acid accumulation, maintaining healthy anti-inflammatory process, improving liver immune function, promoting liver cell regeneration, improving liver renewal function, stimulating bile release, promoting healthy bile flow, liver rejuvenating, or the like of a mammal are also disclosed, wherein the medical composition contains contemplated compositions as an effective ingredient.

BRIEF DESCRIPTION OF THE FIGURES

FIG. 1 shows a HPLC chromatogram of *Artemisia capillaris* 70% ethanol extract.

DETAILED DESCRIPTION

In brief, the present disclosure is directed to compounds and compositions useful for liver health management, including stereoisomers, pharmaceutically or nutraceutically acceptable salts, tautomers, glycosides and prodrugs of the disclosed compounds, and to related methods of improving liver health.

Contemplated compounds and compositions are derived from or comprise at least one plant extract, wherein the plant extract may or may not be enriched. As part of this development, frequently and acceptable models were utilized to test contemplated compounds and compositions. In addition, a therapeutic intervention for liver health was designed by intercepting points in the mechanisms of liver degradation and studying those results. Contemplated compounds, medicinal compositions and compositions are sufficient to effect treatment, including any one or more of: (1) treating or preventing damage of liver cells in a mammal; (2) promoting liver health; (3) preserve detoxification and antioxidation liver enzymes in a mammal; (4) increasing liver detoxification capacity in a mammal; (5) treating or preventing liver diseases in a mammal; (6) modifying inflammation of a liver in a mammal; and (7) improving liver renewal function.

Specifically, compositions, compounds and methods for treatment of and maintaining the health of the liver are disclosed that include a mixture of plant extracts, wherein the plant extracts comprise at least one *Artemisia* extract, at least one *Aloe* gel powder, and at least one *Schizandra* extract.

In addition, compositions, compounds and methods for treatment of and maintaining the health of the liver are disclosed that include a mixture of plant extracts, wherein the plant extracts comprise at least one *Artemisia* extract enriched for at least one polymer or biopolymer, at least one *Aloe* gel powder enriched for at least one chromone, and at least one *Schizandra* extract enriched for at least one lignan and organic acid.

Medical compositions and methods for maintaining liver function, minimizing liver cell damage, promoting healthy liver, protecting liver antioxidation integrity, neutralizing toxins, diminishing the action of free radicals that affecting liver health, scavenging reactive oxygen species, reducing oxidative stress, preventing the formation of toxic metabolisms, improving liver detoxification capacity and/or function, liver cleansing, restoring liver structure, liver protecting liver cells from toxins, helping liver's blood flow and circulation, supporting liver function, fortifying and soothing lever, calming and tonifying liver, alleviating liver pain, purging harmful chemicals and organisms, supporting liver's metabolic process, alleviating liver discomfort, alleviating fatty liver, improving liver detoxification capacity, lowering liver enzymes, providing natural oxidants, increasing SOD, increasing GSH, reducing liver cell peroxidation, reducing fatty acid accumulation, maintaining healthy anti-inflammatory process, improving liver immune function, promoting liver cell regeneration, improving liver renewal function, stimulating bile release, promoting healthy bile flow, liver rejuvenating, or the like of a mammal are also disclosed, wherein the medical composition contains contemplated compositions as an effective ingredient.

The concept of discovering a unique blend of compounds and extracts with enhanced efficacy to protect liver from repeated exposures of oxidative stress was developed keeping alcohol induced liver injury, generalized fatigue and exhaustion in mind. Historically, some botanicals rich in phenolic compounds have been reported to be associated with antioxidative actions in biological systems, acting as scavengers of singlet oxygen and free radicals, leading to their use in herbal medicine. It is contemplated that combining such plant materials having an understood efficacy and safety data would be advantageous for overall liver health. As such, APAP and $CCl_4$ models were utilized to screen various plant extracts. As a result, some plant extracts showed a reduction in serum ALT only in one model, but the criteria for a lead to be considered was to show efficacy in both models.

From a total of 38 plant materials tested, *Schisandra*, *Artemisia* and N931 were the only materials demonstrated their efficacy in both models. N931 is a composition containing a unique combination of 1-4% aloesin and 96-99% 200:1 *Aloe vera* inner leaf fell powder polysaccharides. As disclosed herein, contemplated compositions generally comprise a mixture of plant extracts from an *Artemisia* extract enriched for one or more biopolymers, an *Aloe* gel powder enriched for one or more chromones, and a *Schizandra* extract enriched for one or more lignans and organic acids.

The degrees of inhibitions observed for these materials were not equal between models. For example, while extracts from *Schizandra* seemed to show higher protection of liver injury caused by APAP (up to 48.9% at a dose of 500 mg/kg), at the same dosage the extract showed only 22.8% inhibitions in the $CCl_4$-induced hepatotoxicity model. On the other hand, *Artemisia* extract, such as *Artemisia capillaris* showed 48.0% reduction in serum ALT level at the dose of 400 mg/kg in the $CCl_4$-induced hepatotoxicity model; in contrast, the inhibitions observed in the APAP-induced liver injury model was only 24.0% at this dose level when compared to vehicle control. Given these strong individual performances observed in a separate model for each plant, the idea of combining these plant extracts for a better outcome in both models was reinforced. N931 showed moderate liver protection activity in both models. As disclosed above, considerable studies have attested the antioxidant activities of *Schizandra, Artemisia* and N931 with various degrees of liver protection abilities. However, they were never combined together before at specific ratios to yield contemplated and disclosed compositions, including SAL, which is generally understood as the unique combination of *Schizandra, Artemisia* and N931.

An interesting discovery was that when *Schizandra* was blended with *Artemisia capillaris* at ratios of 4:1, 2:1, 1:1, 1:2 and 1:4 at a dose of 400 mg/kg, only the 2:1 (as twice *Schizandra* than *Artemisia capillaris*) in the APAP model and 1:2 (as twice *Artemisia capillaris* than *Schizandra*) in the $CCL_4$ model showed 48.0% and 40.6% reductions in serum ALT levels, respectively, compared to the vehicle control with injury. They fell short to show the expected efficacy in both models at a single ratio suggesting the need for a third component to complete the composition. N931 was considered to be that component, as it showed moderate inhibition in both models. The addition of N931 to these two lead blends showed liver protection activity in both models at a similar magnitude: i.e. 52.5% and 46.3% in both models, respectively, which was considered an added benefit as a result of the third component of the composition or compound. When the merit of formulating these three plant materials was tested, an unexpected synergy was observed from the combination of these three plant materials that exceeded the predicted result based on simply summing the effects observed for each of its constituents at the given ratio and at the dose of 400 mg/kg.

In fact, none of the constituents showed liver protection activity at the magnitude equivalent to the one shown for a contemplated compound or composition comprising *Schizandra, Artemisia* and N931. Furthermore, data from liver panel that includes AST, ALT, bile acid, total protein, total bilirubin, conjugated bilirubin, albumin, and total protein showed that contemplated compositions comprise liver protection activity when compared to the vehicle treated control animals with injury. As data from the liver homogenate reflected, contemplated compositions, including SAL, also replenished the depleted hepatic glutathione in association with an increased activity in hepatic superoxide dismutase. A contemplated and unique ratio of 4S:8A:3L provides demonstrated liver protection activity in multiple animal models in association with several oxidative stress specific biomarkers moderations.

As disclosed herein, the *Artemisia* extract and the *Schizandra* extract can be blended in a weight ratio from 4:1 to 1:4. In some contemplated embodiments, the *Aloe* gel powder can be further blended with a mixture of *Artemisia* and *Schizandra* extracts in a weight percentage of about 5% to about 50%. In other contemplated embodiments, the mixture of *Artemisia, Schizandra* and *Aloe* leaf gel powder may be provided in a ratio of 8:4:3, respectively.

*Schizandra* extract is a contemplated component or constituent that can be utilized as part of a target compound or composition. *Schizandra* extract may be obtained from any suitable source, including *Schisandra chinensis, Schisandra elongate, Schisandra glabra, Schisandra glaucescens, Schisandra henryi, Schisandra incarnate, Schisandra lancifolia, Schisandra neglecta, Schisandra nigra, Schisandra propinqua, Schisandra pubescens, Schisandra repanda, Schisandra rubriflora, Schisandra rubrifolia, Schisandra sinensis, Schisandra sphaerandra, Schisandra sphenanthera, Schisandra tomentella, Schisandra tuberculata, Schisandra vestita, Schisandra viridis, Schisandra wilsoniana* or a combination thereof.

*Schizandra* extract may be enriched for one or more lignans and organic acids, as contemplated herein. Contemplated lignans isolated from *Schizandra* extract is Schisandrin, Deoxyschizandrin, γ-Schizandrin, Pseudo-γ-schizandrin, Wuweizisu B, Wuweizisu C, Isoschizandrin, Pregomisin, eoschizandrin, Schizandrol, Schizandrol A, Schizandrol B, Schisantherin A, B, C, D, E, Rubschisantherin, Schisanhenol acetdte, Schisanhenol B, Schisanhenol, Gomisin A, B, C, D, E, F, G, H, J, N, O, R, S, T, U, Epigomisin O, Angeloylgomisin H, O, Q, T, igloylgomisin H, P, Angeloyisogomisin O, Benzoyl-gomisin H, O, P, Q, Benzoyl-isogomisin or a combination thereof. Contemplated organic acids isolated from a *Schizandra* extract include malic acid, citric acid, shikimic acid or a combination thereof.

*Artemisia* extract is a contemplated component or constituent that can be utilized as part of a target compound or composition. *Artemisia* extract may be obtained from any suitable source, including *Artemisia absinthium, Artemisia abrotanum* L., *Artemisia afra, Artemisia annua* L, *Artemisia arborescens, Artemisia asiatica, Artemisia campestris, Artemisia deserti, Artemisia iwayomogi, Artemisia ludoviciana, Artemisia vulgaris, Artemisia oelandica, Artemisia princeps* Pamp, *Artemisia sacrorum, Artemisia scoparia, Artemisia stelleriana, Artemisia frigida* Willd, *Artemisia anethoides* Mattf., *Artemisia anethifolia* Weber., *Artemisia faurier* Nakai, *Origanum vulgare, Siphenostegia chinensis*, or any combination thereof.

*Artemisia* extract may be enriched for one or more biopolymers, as contemplated herein. Contemplated polymers and biopolymers isolated from *Artemisia* extract are extracted with any suitable solvent, including water, methanol, ethanol, alcohol, a water-mixed solvent or a combination thereof. In contemplated embodiments, the *Artemisia* extract comprises about 0.01% to about 99.9% biopolymers with individual or a median molecular weights higher than about 500 g/mol. In some contemplated embodiments, the *Artemisia* extract comprises about 0.01% to about 99.9% biopolymers with individual or a median molecular weights higher than about 750 g/mol. In other contemplated embodiments, the *Artemisia* extract comprises about 0.01% to about 99.9% biopolymers with individual or a median molecular weights higher than about 1000 g/mol.

*Aloe* gel powder is another contemplated component or constituent and may be provided by any suitable source, including *Aloe arborescens, Aloe barbadensis, Aloe cremnophila, Aloe ferox, Aloe saponaria, Aloe vera, Aloe vera* var. *chinensis* or a combination thereof.

*Aloe* gel powder may be enriched for one or more chromones, as contemplated herein. Contemplated chromones comprise or are selected from aloesin, aloesinol, aloeresin A, aloeresin B, aloeresin C, aloeresin D, aloeresin E or any combination thereof. In contemplated embodiments, the at least one chromone composition may comprise about 0.01% to about 100% of one or more chromones. In some contemplated embodiments, the chromone composition comprises about 1% to about 4% of Aloesin, wherein the composition is essentially free of anthroquinones and wherein the *Aloe* gel is isolated from a plant selected from *Aloe barbadensis* or *Aloe vera*; and wherein the at least one chromone is isolated from *Aloe vera* or *Aloe ferox* or any combination thereof.

Contemplated compounds, medicinal compositions and compositions may comprise or additionally comprise or consist of at least one liver protectant. In some embodiments, the at least one liver protectant may comprise or consist of plant powder or plant extract of milk thistle, *curcuma, bupleurum*, licorice, *salvia, morus, hovenia, agrimony, cudrania, lyceum*, citrus, *prunus*, yellow mume, Korea gim, dandelion, *vitis*, grape seed, *rubus, camellia*, green tea, krill oil, yeast, soy bean; isolated and enriched silymarins, flavonoids, phospholipids, thios, pycnogenols, gelatins, soy lecithin, pancreatic enzymes; natural or synthetic N-acetyl-cysteine, taurine, riboflavin, niacin, pyridoxine, folic acid, carotenes, vitamin A, vitamin B2, B6, B16, vitamin C, vitamin E, glutathione, branched-chain amino acids, selenium, copper, zinc, manganese, coenzyme Q10, L-arginine, L-glutamine, phosphatidylcholine or the like and or a combination thereof.

Also contemplated herein are in vivo metabolic products of the disclosed compounds. Such products may result from, for example, the oxidation, reduction, hydrolysis, amidation, esterification, and the like of the administered compound, primarily due to enzymatic processes. Accordingly, contemplated compounds are those produced by a process comprising administering a contemplated compound or composition to a mammal for a period of time sufficient to yield a metabolic product thereof. Such products are typically identified by administering a radiolabelled compound of this disclosure in a detectable dose to an animal, such as rat, mouse, guinea pig, dog, cat, pig, sheep, horse, monkey, or human, allowing sufficient time for metabolism to occur, and then isolating its conversion products from the urine, blood or other biological samples.

As used herein, the phrases "stable compound" and "stable structure" are used interchangeably and used to indicate a compound that is sufficiently robust to survive isolation to a useful degree of purity from a reaction mixture, and to survive formulation into an efficacious therapeutic agent.

As used herein, the term "mammal" includes humans and both domestic animals, such as laboratory animals or household pets (e.g., rat, mouse, guinea pig, cats, dogs, swine, cattle, sheep, goats, horses, rabbits, primates), and non-domestic animals, such as wildlife or the like.

As used herein, the terms "optional" or "optionally" may be used interchangeably and mean that the subsequently described element, component, event or circumstances may or may not occur, and includes instances where the element, component, event or circumstance occur and instances in which they do not. For example, "optionally substituted aryl" means that the aryl radical may or may not be substituted—in other words, the description includes both substituted aryl radicals and aryl radicals having no substitution.

Contemplated compounds, medicinal compositions and compositions may comprise or additionally comprise or consist of at least one pharmaceutically or nutraceutically acceptable carrier, diluent or excipient. As used herein, the phrase "pharmaceutically or nutraceutically acceptable carrier, diluent or excipient" includes any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Contemplated compounds, medicinal compositions and compositions may comprise or additionally comprise or consist of at least one pharmaceutically or nutraceutically acceptable salt. As used herein, the phrase "pharmaceutically or nutraceutically acceptable salt" includes both acid addition and base addition salts.

As used herein, the phrase "pharmaceutically or nutraceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, or the like.

As used herein, the phrase "pharmaceutically or nutraceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include the sodium, potassium, lithium, ammonium, calcium, magnesium, iron, zinc, copper, manganese, aluminum salts and the like. In certain embodiments, the inorganic salts are ammonium, sodium, potassium, calcium, or magnesium salts. Salts derived from organic bases include salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly useful organic bases include isopropylamine, diethylamine, ethanolamine, trimethylamine, dicyclohexylamine, choline, or caffeine.

Often crystallizations produce a solvate of or include contemplated compounds. As used herein, the term "solvate" refers to an aggregate that comprises one or more molecules of a contemplated compound, medicinal composition or composition with one or more molecules of solvent. The solvent may be water, in which case the solvate may be a hydrate. Alternatively, the solvent may be an organic solvent. Thus, the contemplated compounds, medicinal compositions or compositions may exist as a hydrate, including a monohydrate, dihydrate, hemihydrate, sesquihydrate, trihydrate, tetrahydrate and the like, as well as the corresponding solvated forms. A contemplated compound, medicinal composition or composition may be a true solvate, while in other cases, a contemplated compound, medicinal composition or composition may merely retain adventitious water or be a mixture of water plus some adventitious solvent.

A "pharmaceutical composition" or "nutraceutical composition" refers to a formulation of a contemplated compound, medicinal composition or composition and a medium generally accepted in the art for the delivery of the biologically active compound to mammals, e.g., humans. For example, a contemplated pharmaceutical compound, medicinal composition or composition may be formulated or used as a stand-alone composition, or as a component in a prescription drug, an over-the-counter (OTC) medicine, a botanical drug, an herbal medicine, a homeopathic agent, or any other form of health care product reviewed and approved by a government agency. Exemplary and contemplated nutraceutical compositions may be formulated or used as a stand-alone composition, or as a nutritional or bioactive component in food, a novel food, a functional food, a beverage, a bar, a food flavor, a food additive, a medical food, a dietary supplement, or an herbal product. A medium generally accepted in the art includes all pharmaceutically or nutraceutically acceptable carriers, diluents or excipients therefor.

As used herein, the phrase "enriched for" refers to a plant extract or other preparation having at least about a two-fold up to about a 1000-fold increase in the amount or activity of one or more active compounds as compared to the amount or activity of the one or more active compounds found in the weight of the plant material or other source before extraction or other preparation. In certain embodiments, the weight of the plant material or other source before extraction or other preparation may be dry weight, wet weight, or a combination thereof.

As used herein, "major active ingredient" or "major active component" refers to one or more active contemplated compounds found in a plant extract or other preparation, or enriched for in a plant extract or other preparation, which is capable of at least one biological activity. In certain embodiments, a major active ingredient of an enriched extract will be the one or more active compounds that were enriched in that extract. Generally, one or more major active components will impart, directly or indirectly, most (i.e., greater than 50%) of one or more measurable biological activities or effects as compared to other extract components. In certain embodiments, a major active ingredient may be a minor component by weight percentage of an extract (e.g., less than about 50%, 25%, 20%, 15%, 10%, 5%, or 1% of the components contained in an extract) but still provide most of the desired biological activity. Any contemplated composition containing a major active ingredient may also contain minor active ingredients that may or may not contribute to the pharmaceutical or nutraceutical activity of the enriched composition, but not to the level of major active components, and minor active components alone may not be effective in the absence of a major active ingredient.

As used herein, the phrases "effective amount" or "therapeutically effective amount" refer to that amount of a contemplated compound, medicinal composition or composition that, when administered to a mammal, such as a human, is sufficient to effect treatment, including any one or more of: (1) treating or preventing damage of liver cells in a mammal; (2) promoting liver health; (3) preserve detoxification and anti-oxidation liver enzymes in a mammal; (4) increasing liver detoxification capacity in a mammal; (5) treating or preventing liver diseases in a mammal; (6) modifying inflammation of a liver in a mammal; and (7) improving liver renewal function. The amount of a contemplated compound, medicinal composition or composition that constitutes a "therapeutically effective amount" will vary depending on the compound, the condition being treated and its severity, the manner of administration, the duration of treatment, or the body weight and age of a subject to be treated, but can be determined by one of ordinary skill in the art having regard to his own knowledge and to this disclosure.

"Supplements", as used herein, refers to a product, compound and/or composition that improves, promotes, supports, increases, regulates, manages, controls, maintains, optimizes, modifies, reduces, inhibits, or prevents a particular condition, structure or function associated with a natural state or biological process (i.e., are not used to diagnose, treat, mitigate, cure, or prevent disease). In certain embodiments, a supplement is a dietary supplement. For example, with regard to liver health-related conditions, dietary supplements may be used for maintaining liver function, minimizing liver cell damage, promoting healthy liver, protecting the liver's antioxidation integrity, neutralizing toxins, diminishing the action of free radicals that affecting liver health, scavenging reactive oxygen species, reducing oxidative stress, preventing the formation of toxic metabolisms, improving liver detoxification capacity and/or function, liver cleansing, restoring liver structure, protecting liver cells from toxins, helping the liver's blood flow and circulation, supporting liver function, fortifying and soothing the liver, calming and tonifying the liver, alleviating liver pain, purging harmful chemicals and organisms, supporting the liver's metabolic process, alleviating liver discomfort, alleviating fatty liver, improving liver detoxification capacity, lowering liver enzymes, providing natural oxidants, increasing SOD, increasing GSH, reducing liver cell peroxidation, reducing fatty acid accumulation, maintaining healthy anti-inflammatory process, improving liver immune function, promoting liver cell regeneration, improving liver renewal function, stimulating bile release, promoting healthy bile flow, liver rejuvenating, or the like of a mammal. In certain embodiments, dietary supplements are a special category of diet, food or both and are not a drug.

The terms "treating" or "treatment" or "ameliorating" may be used interchangeably and refer to either a therapeutic treatment or prophylactic/preventative treatment of a disease or condition of interest in a mammal, such as a human, having or suspected of having a disease or condition of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition, (e.g., relieving pain, reducing inflammation, reducing loss of detoxification capacity) without addressing the underlying disease or condition.

As used herein, the terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. In certain embodiments, contemplated compounds, medicinal compositions, compositions and methods are used to treat, for example, hepatitis, alcohol liver diseases, cirrhosis or both.

As used herein, "statistical significance" refers to a p value of 0.050 or less as calculated using the Students t-test and indicates that it is unlikely that a particular event or result being measured has arisen by chance.

The chemical naming protocol and any structure diagrams used herein are a modified form of the I.U.P.A.C. nomenclature system, using the ACD/Name Version 9.07 software program or ChemDraw Ultra Version 11.0 software naming program (CambridgeSoft), wherein the compounds of this disclosure are named herein as derivatives of the central core structure, e.g., the imidazopyridine structure. For complex chemical names utilized herein, a substituent group is named before the group to which it attaches. For example, cyclopropylethyl comprises an ethyl backbone with cyclopropyl substituent.

In certain embodiments, contemplated compounds and compositions (e.g., pharmaceutical, nutraceutical) may be administered in an amount sufficient to promote liver health; improve liver health; maintain liver health; treat or manage liver health; support liver health; support a normal and comfortable range of liver detox function; improve free radical clearance capacity of liver; reduce the damage of harmful free radicals derived from chemicals, drugs, metabolites, and biological toxins; preserve enzymes that affect liver health, protects from chronic oxidative stress caused liver injury due to Hepatitis B/C virus infection, alcohol consumption, metabolic disorders, non-alcoholic fatty liver disease (NAFLD), non-alcoholic steatohepatitis (NASH), alcoholic liver disease, hepatic encephalopathy, liver fibroproliferative disease (hepatic fibrosis), hepatocyte injury during hypoxia/reoxygenation, or any combination thereof; or any other associated indication described herein, and generally with acceptable toxicity to a patient.

In certain other embodiments, contemplated compounds and compositions (e.g., pharmaceutical, nutraceutical) may be administered in an amount sufficient to treat a liver disorder or disease comprising viral hepatitis, alcohol hepatitis, autoimmune hepatitis, alcohol liver disease, fatty liver disease, steatosis, steatohepatitis, non-alcohol fatty liver disease, drug-induced liver disease, cirrhosis, fibrosis, liver failure, drug induced liver failure, metabolic syndrome, hepatocellular carcinoma, cholangiocarcinoma, primary biliary cirrhosis, bile capillaries, Gilbert's syndrome, jaundice, or any other liver toxicity associated indication or combination thereof, and generally with acceptable toxicity to a patient.

Administration of contemplated compounds, medicinal compositions or compositions, or their pharmaceutically or nutraceutically acceptable salts, in pure form or in an appropriate pharmaceutical or nutraceutical composition, can be carried out via any of the accepted modes of administration of agents for serving similar utilities. Contemplated pharmaceutical or nutraceutical compositions can be prepared by combining a contemplated compound with an appropriate pharmaceutically or nutraceutically acceptable carrier, diluent or excipient, and may be formulated into preparations in solid, semi solid, liquid or gaseous forms, such as tablets, capsules, powders, granules, ointments, solutions, suppositories, injections, inhalants, gels, microspheres, and aerosols. Typical routes of administering such pharmaceutical or nutraceutical compositions include oral, topical, transdermal, inhalation, parenteral, sublingual, buccal, rectal, vaginal, or intranasal.

The term "parenteral", as used herein, includes subcutaneous injections, intravenous, intramuscular, intrasternal injection or infusion techniques. Contemplated pharmaceutical or nutraceutical compositions are formulated so as to allow the active ingredients contained therein to be bioavailable upon or soon after administration of the composition to a patient. In some embodiments, contemplated compositions and compounds may be designed or formulated so that they may be time-released after administration.

In certain embodiments, contemplated compositions are administered to a subject or patient in the form of one or more dosage units, where, for example, a tablet may be a single dosage unit, and a container of a contemplated compound in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). A contemplated composition to be administered will, in any event, contain a therapeutically effective amount of a contemplated compound, or a pharmaceutically or nutraceutically acceptable salt thereof, for treatment of a disease or condition of interest in accordance with the teachings of this disclosure.

A contemplated pharmaceutical or nutraceutical composition may be in the form of a solid or liquid. In one aspect, the carrier(s) are particulate, so that the compositions are, for example, in tablet or powder form. The carrier(s) may be liquid, with the compositions being, for example, oral syrup, injectable liquid or an aerosol, which is useful in, for example, inhalatory administration.

When intended for oral administration, the pharmaceutical or nutraceutical composition is in either solid or liquid form, where semi solid, semi liquid, suspension and gel forms are included within the forms considered herein as either solid or liquid.

As a solid composition for oral administration, the pharmaceutical or nutraceutical composition may be formulated into a powder, granule, compressed tablet, pill, capsule, chewing gum, wafer, bar, or like form. Such a solid composition will typically contain one or more inert diluents or edible carriers. In addition, one or more of the following may be present: binders such as carboxymethylcellulose, ethyl cellulose, cyclodextrin, microcrystalline cellulose, gum tragacanth or gelatin; excipients such as starch, lactose or dextrins, disintegrating agents such as alginic acid, sodium alginate, Primojel®, corn starch and the like; lubricants such as magnesium stearate or Sterotex®; glidants such as colloidal silicon dioxide; sweetening agents such as sucrose or saccharin; a flavoring agent such as peppermint, methyl salicylate or orange flavoring; and a coloring agent.

When the pharmaceutical or nutraceutical composition is in the form of a capsule, for example, a gelatin capsule, it may contain, in addition to materials of the above type, a liquid carrier such as polyethylene glycol or oil.

A contemplated pharmaceutical or nutraceutical composition may be in the form of a liquid, for example, an elixir, syrup, gel, solution, emulsion or suspension. The liquid may be for oral administration or for delivery by injection, as two examples. When intended for oral administration, a useful composition contains, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A contemplated liquid pharmaceutical or nutraceutical compositions, whether they be solutions, suspensions or other like form, may include one or more of the following adjuvants: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a generally useful adjuvant. An injectable pharmaceutical or nutraceutical composition is sterile.

A contemplated liquid pharmaceutical or nutraceutical composition intended for either parenteral or oral administration should contain an amount of a contemplated compound, medicinal composition or composition such that a suitable dosage will be obtained.

A contemplated pharmaceutical or nutraceutical composition may be intended for topical administration, in which case the carrier may suitably comprise a solution, emulsion, cream, lotion, ointment, or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical or nutraceutical composition for topical administration. If intended for transdermal administration, the composition may include a transdermal patch or iontophoresis device.

A contemplated pharmaceutical or nutraceutical composition may be intended for rectal administration, in the form, for example, of a suppository, which will melt in the rectum and release the drug. The composition for rectal administration may contain an oleaginous base as a suitable nonirritating excipient. Such bases include lanolin, cocoa butter and polyethylene glycol.

A contemplated pharmaceutical or nutraceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

A contemplated pharmaceutical or nutraceutical composition in solid or liquid form may include an agent that binds to the contemplated compound and thereby assists in the delivery of the compound. Suitable agents that may act in this capacity include a monoclonal or polyclonal antibody, a protein or a liposome.

A contemplated pharmaceutical or nutraceutical composition in solid or liquid form may include reducing the size of a particle to, for example, improve bioavailability. The size of a powder, granule, particle, microsphere, or the like in a composition, with or without an excipient, can be macro (e.g., visible to the eye or at least 100 μm in size), micro (e.g., may range from about 100 μm to about 100 nm in size), nano (e.g., may no more than 100 nm in size), and any size in between or any combination thereof to improve size and bulk density.

A contemplated pharmaceutical or nutraceutical composition may comprise or consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of this disclosure may be delivered in single phase, bi phasic, or tri phasic systems in order to deliver the active ingredient(s). Delivery of the aerosol includes the necessary container, activators, valves, subcontainers, and the like, which together may form a kit. One skilled in the art, without undue experimentation, may determine the most appropriate aerosol(s).

A contemplated pharmaceutical or nutraceutical composition may be prepared by methodology well known in the pharmaceutical or nutraceutical art. For example, a pharmaceutical or nutraceutical composition intended to be administered by injection can be prepared by combining a contemplated compound with sterile, distilled water so as to form a solution. A surfactant may be added to facilitate the formation of a homogeneous solution or suspension. Surfactants are compounds that non-covalently interact with a contemplated compound so as to facilitate dissolution or homogeneous suspension of the compound in the aqueous delivery system.

Contemplated compounds, compositions and medicinal compositions, or their pharmaceutically or nutraceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Contemplated compounds, compositions and medicinal compositions, or pharmaceutically or nutraceutically acceptable derivatives thereof, may also be administered simultaneously with, prior to, or after administration of one or more other therapeutic agents. Such combination therapy includes administration of a single pharmaceutical or nutraceutical dosage formulation that contains a contemplated compound and one or more additional active agents, as well as administration of a contemplated compound and each active agent in its own separate pharmaceutical or nutraceutical dosage formulation. For example, a contemplated compound and another active agent can be administered to the patient together in a single oral dosage composition, such as a tablet or capsule, or each agent can be administered in separate oral dosage formulations. Where separate dosage formulations are used, contemplated compounds and one or more additional active agents can be administered at essentially the same time, i.e., concurrently, or at separate staggered times, i.e., sequentially; combination therapy is understood to include all these regimens.

It is understood that in the present description, combinations of substituents or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include C(O)R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley, which is incorporated by reference herein in its entirety. As one of skill in the art would appreciate, a protecting group may also be a polymer resin such as a Wang resin, Rink resin or a 2-chlorotrityl-chloride resin.

It will also be appreciated by those skilled in the art, although such protected derivatives of contemplated compounds may not possess pharmacological activity as such, they may be administered to a mammal and thereafter metabolized in the body to form compounds which are pharmacologically active. Such derivatives may therefore be described as "prodrugs". All prodrugs of contemplated compounds are included within the scope of this disclosure.

Furthermore, contemplated compounds that exist in free base or acid form can be converted to their pharmaceutically or nutraceutically acceptable salts by treatment with the appropriate inorganic or organic base or acid by methods known to one skilled in the art. Salts of contemplated compounds can be converted to their free base or acid form by standard techniques.

In some embodiments, contemplated compounds, compositions and/or medicinal compositions can be isolated from plant sources, for example, from those plants included in the Examples and elsewhere throughout the present application. Suitable plant parts for isolation of contemplated extracts and compounds include leaves, bark, trunk, trunk bark, stems, stem bark, twigs, tubers, root, root bark, bark surface (such as periderm or polyderm, which may include phellem, phellogen, phelloderm, or any combination thereof), young shoots, rhizomes, seed, fruit, androecium, gynoecium, calyx, stamen, petal, sepal, carpel (pistil), flower, or any combination thereof. Contemplated plant extracts are derived from at least one plant part selected from the group consisting of stems, stem barks, trunks, trunk barks, twigs, tubers, roots, root barks, young shoots, seeds, rhizomes, flowers and other reproductive organs, leaves, other aerial parts or a combination thereof. In some related embodiments, contemplated compounds are isolated from plant sources and synthetically modified to contain any of the recited substituents. In this regard, synthetic modification of contemplated compounds isolated from plants can be accomplished using any number of techniques that are known in the art and are well within the knowledge of one of ordinary skill in the art.

EXAMPLES

Example 1

Animals

Purpose bred mice at the age of 7-8 weeks with body weight of 25-30 g were purchased form Charles River Laboratories (Wilmington, Mass.). Animals were acclimated upon arrival for a week before being weighed and assigned randomly to their respective groups. ICR mice (5/cage) were housed in a polypropylene cage and individually identified by numbers on their tail. Each cage was covered with wire bar lid and filtered top (Allentown, N.J.). Each individual cage was identified with a cage card indicating project number, test article, dose level, group, and an animal number. The Harlan T7087 soft cob bedding was used and changed at least twice weekly. Animals were provided with fresh water and rodent chow diet #T2018 (Harlan Teklad, 370W, Kent, Wash.) ad libitum and were housed in a temperature controlled room (22.2° C.) on a 12-hour light-dark cycle. All animal experiments were conducted according to institutional guidelines congruent with guide for the care and use of laboratory animals.

Example 2

Acetaminophen (APAP) or Carbon Tetrachloride (CCL4)-Induced Liver Damage Animal Models A balanced therapeutic schedule was generated and optimized as follows to address prophylaxis and intervention: for APAP-induced hepatotoxicity model, APAP (Lot #MKBQ8028V, from Sigma) at a dose of 400 mg/kg dissolved in warm saline (Lot #132908 from G-Biosciences, Lot #720729 from Quality Biological) (heated to 60° C. and cooled down to ambient temperature) was orally administered to overnight fasted ICR/CD-1 mice to induce toxicity. For the $CCl_4$-induced hepatotoxicity model, $CCl_4$ (Lot #SHBD5351V, from Sigma) at a dose of 25 µl/kg dissolved in corn oil was administered intraperitoneally to overnight fasted ICR/CD-1 mice to induce toxicity. For both models, materials were administered at −48 hr, −24 hr, −2 hr before APAP or $CCl_4$ administrations and +6 hr after induction. In total, the mice received 3 doses before the chemical induction and a dose after the chemical induction. 10% Tween-20 (Lot #0134C141 from Amresco), 1% CMC (Lot #NH0454 from Spectra) or 1% MC (Lot #SLBK4357V) were used as a carrier vehicle for all the materials. Control mice without APAP or $CCl_4$ received carrier vehicle only. Serum ALT was determined at T24 (Phoenix Laboratories, Everett, Wash.).

Example 3

Preparation of Plant Extracts

Plants were collected and prepared with different solvents based on their active compounds properties and screened in our hepatotoxicity animal models in mice. The following 19 plants in Table 1, including different parts from 16 species, showed serum ALT inhibition at different levels either in acetaminophen induced model or $CCl_4$ induced model in mice. Only plants with efficacies in both models will be selected for further studies.

Milk thistle extracts were produced as 80% ethanol/20% water extracts of Silybum marianum seeds with an extraction ratio of 40-50:1. The ground seed was extracted with 80% ethanol/20% water, and then the cake was separated from the supernatant by filtration. The solvent was removed in vavuo to give a soft extract, which was mixed with maltodextrin and further dried with spray dryer. Milk thistle extracts was standardized to meet specification of no less than 50% total silymarins and no less than 30% silybinin. Silymarin is made up of a mixture of flavonolignans silibinin, silidianin, and silicristin. Silibinin is the major active constituent of silymarin. Standardized extract of the milk thistle seeds is commercially available.

As disclosed earlier, N931 is a composition containing a unique combination of 1-4% aloesin and 96-99% 200:1 *Aloe vera* inner leaf gel powder polysaccharides blended via a conventional method. *Aloe vera* inner leaf gel powder polysaccharides were supplied by Aloecorp in the form of the lyophilizate. The rind was removed manually from the fresh cleaned leaves of the *Aloe barbadensis* plant, and then the aloe juice was collected and treated with cellulase to deactivate the enzyme. Activated Charcoal was used to remove the color during the enzyme deactivation. The decolorized filtrate was further transfer into the lyophilization traps to give the *Aloe vera* inner leaf gel power, which is blended with 1-4% aloesin to make N931.

TABLE 1

Summary of plant extracts for in vivo liver protection evaluation

| Plant Name | Code | Plant Part | Extraction Method | Extraction Yield | Marker Content |
|---|---|---|---|---|---|
| *Silybum marianum* | — | Seeds | 80% EtOH extract | 40-50:1 | 32%-66% Silymarin |
| N931 | N931 | leaf | Whole leaf gel | 200:1 | 1-4% Aloesin |
| *Morus alba* | E1374 | fruit | water extract | 4:1 | — |
| *Morus alba* | E1375 | leaf | extract | 10:1 | DNJ 1% |
| *Morus alba* | RM605 | root bark | 70% ethanol extract | 14.7% | NLT 7% actives |
| *Morua alba* | E1377 | stem | water extract | 10:1 | — |
| *Cudrania tricuspidata* | RN417-01-01 | leaf | 70% ethanol extract | — | — |
| *Hovenia dulcis* | E1388 | fruit | water extract | 10:1 | — |
| *Artemisia capillaris* | R00594 | aerial parts | 70% ethanol extract | 20.9% | NLT 3% chlorogenic acid, NLT 6% total chlorogenic acids |
| *Schizandra chinensis* | L0498 | Fruit | 70% extract | 17.4% | 2% schizandrins |
| *Citrus reticulata* | R00590 | Pericarpium | 70% ethanol extract | 40.1% | — |
| *Gynostemma pentaphyllum* | R00596 | whole plant | 70% ethanol extract | 21.5% | — |
| *Agrimonia eupatoria* | E1399 | leaf | 40% extract | — | Luteolin 7-glucuronide 3.2 ± 0.64 mg/g |
| *Paeonia lactiflora* | L0503 | roots | extract | — | 10% paeoniflorin |

Example 4

Liver Protection Activity of Plant Extracts on APAP and CCL4-Induced Hepatotoxicity Model Plant materials from legacy mining collected based on their historical usage on liver protection and renewal were extracted using 70% ethanol and screened for their efficacy in both APAP and $CCl_4$-induced liver toxicity. Materials were administered to animals orally at a dosage specified in Tables 2-3. While most plant extracts showed inhibition of serum ALT in one model, a few plants demonstrated their efficacy in both models. Among those, *Schizandra chinensis*, *Artemisia capillaris*, Milk thistle and Loesyn were selected for further studies.

TABLE 2

Percent inhibition of serum ALT for plant extracts in $CCl_4$-induced liver toxicity model

| Plant Name | Plant Part | Code | Dosage (mg/kg) | % inhibition of ALT | p-values |
|---|---|---|---|---|---|
| *Agrimonia eupatoria* | leaf | E1399 | 500 | 67.6 | |
| Milk thistle | seeds | F140520008 | 200 | 39.0 | 0.04 |
| N931 (2% Alosin) | leaf | QMA2 | 400 | 40.5 | 0.01 |
| *Citrus reticulata* | pericarpium | R00590 | 500 | 22.4 | 0.29 |
| *Raphanus sativus* | seed | R00593 | 500 | 6.4 | 0.76 |
| *Artemisia capillaris* (lab scale) | whole plant | R00594 | 500 | 24.4 | 0.20 |
| *Crataegus pinnatifida* | fruit | R00595 | 500 | 1.3 | 0.95 |
| *Gynostemma pentaphyllum* | whole plant | R00596 | 500 | 23.3 | 0.29 |
| *Angelica sinensis* | roots | L0495 | 500 | 10.6 | 0.38 |
| *Schizandra chinensis* | fruit | L0498 | 400 | 38.1 | 0.04 |
| *Lycium barbarum* | fruit | L0505 | 500 | 6.5 | 0.68 |
| *Paeonia lactiflora* | roots | L0503 | 500 | 23.3 | 0.09 |
| *Dolicho LablabL.* | seed | R00601 | 500 | 17.7 | 0.20 |
| Korean Gim extract (*Porphyra* sp) | sea weed | E1387 | 500 | 6.7 | 0.17 |
| *Artemisia capillaris* | whole plant | R0684 | 400 | 42.7 | 0.01 |
| *Artemisia dracunculus* | leaf | R0637 | 500 | 28.92 | 0.14 |

TABLE 3

Percent inhibition of serum ALT for plant extracts in APAP-induced liver toxicity model

| Plant Name | Plant Part | CODE | Dosage (mg/kg) | % inhibition of ALT | P-value |
|---|---|---|---|---|---|
| Milk thistle | Seeds | F140520008 | 100 | 23.6 | 0.35 |
| Loesyn (2%) | leaf | QMA2 | 400 | 30.7 | 0.28 |
| Cudrania tricuspidata (leaf) | leaf | RN417-01-01/02 | 500 | 82.0 | 0.001 |
| Agrimonia eupatoria | leaf | E1399 | 500 | 13.1 | 0.61 |
| Hovenia dulcis | — | E1388 | 500 | 93.9 | 0.001 |
| Schizandra chinensis (2%) | fruit | L0498 | 400 | 41.4 | 0.04 |
| Morus alba | stem | E1377 | 500 | 51.5 | 0.05 |
| Morus alba | leaves/twig | E1375 | 500 | 40.4 | 0.01 |
| Morus alba | fruit | E1374 | 1000 | 51.5 | 0.005 |
| Korean Gim extract (Porphyra sp) | seaweed | E1387 | 500 | 6.9 | 0.84 |
| Artemisia capillaris | whole plant | R00594 | 500 | 47.0 | 0.02 |
| Taraxacum officinale | young leaf | R00628 | 500 | 21.8 | 0.38 |
| Taraxacum officinale | roots | R00640 | 500 | 16.9 | 0.48 |

Example 5

Dose-Response Effect of Selected Plant Extracts in APAP Model

Morus leaf (E1375), Morus fruit (E1374), Morus stem (E1377), Artemisia capillaris (R0594), and Schizandra chinensis (2%) (L0498) were tested at doses of 100, 200 and 300 mg/kg in APAP-induced hepatotoxicity model as the method described above. 10% tween 20 was used as a carrier vehicle for all the materials. Control mice without APAP received vehicle (10% tween 20) only. Serum ALT was determined at T24. As seen in the Table 4 below, two plant materials such Schizandra chinensis (2%) (L0498) and Artemisia capillaris (R0594) showed 36.8%, and 32.2% inhibitions in serum ALT level, respectively, at a dose of 300 mg/kg. These reductions were statistically significant. While L0498 showed a 100% survival rate at a dose of 300 mg/kg, R0594 had a 90% survival rate. At the lowest dose (100 mg/kg), L0498 showed only a 30% survival rate. Whereas, R0594 had 70% survival rate at this dose. Regardless of the dose, survival rates in all Morus extracts were as low as 40. These high mortality rates led to inconclusive percent reductions in serum ALT levels. Hence, Schizandra chinensis (2%) (L0498) and Artemisia capillaris (R0594) could be considered as true hits in this model with optimum efficacy at about 300 mg/kg.

TABLE 4

Dose-response study using APAP induced hepatotoxicity model summary

| Group | N | Material | Code | Part | Dose | APAP | % | P- | Survival |
|---|---|---|---|---|---|---|---|---|---|
| G-1 | 5 | Control (−) | — | — | 0 | 0 | — | — | 100 |
| G-2 | 10 | Acetaminophen | APAP | — | 0 | 400 | — | — | 80 |
| G-3 | 10 | Morus alba | E1374 | Fruit | 300 | 400 | 26.6 | 0.07 | 70 |
| G-4 | 10 | | E1374 | | 200 | 400 | 25.6 | 0.15 | 70 |
| G-5 | 10 | | E1374 | | 100 | 400 | 24.0 | 0.15 | 80 |
| G-6 | 10 | | E1375 | Leaf | 300 | 400 | 32.8 | 0.24 | 60 |
| G-7 | 10 | | E1375 | | 200 | 400 | 31.9 | 0.02 | 70 |
| G-8 | 10 | | E1375 | | 100 | 400 | 14.7 | 0.5 | 50 |
| G-9 | 10 | | E1377 | Stem | 300 | 400 | 7.3 | 0.54 | 40 |
| G-10 | 10 | | E1377 | | 200 | 400 | 26.3 | 0.11 | 60 |
| G-11 | 10 | | E1377 | | 100 | 400 | 22.4 | 0.09 | 60 |
| G-12 | 10 | Schisandra | L0498 | Fruit | 300 | 400 | 36.8 | 0.008 | 100 |
| G-13 | 10 | chinensis | L0498 | | 200 | 400 | 8.5 | 0.68 | 80 |
| G-14 | 10 | | L0498 | | 100 | 400 | 55.9 | 0.004 | 30 |
| G-15 | 10 | Artemisia | R0594 | Whole | 300 | 400 | 32.2 | 0.04 | 90 |
| G-16 | 10 | capillaris | R0594 | | 200 | 400 | 21.0 | 0.16 | 90 |
| G-17 | 10 | | R0594 | | 100 | 400 | 10.7 | 0.66 | 70 |

Example 6

Dose-Response Effect of Selected Plant Extracts in $CCl_4$ Model

Agrimonia eupatoria (E1399) and Loesyn (QMA2) at doses of 400 mg/kg, 300 mg/kg and 200 mgkg; Artemisia capillaris (R0594), and Schizandra chinensis (2%) (L0498) at doses of 400 mg/kg and 300 mg/kg were tested on $CCl_4$-induced hepatotoxicity model as described above. 10% Tween-20 was used as a carrier vehicle for all the materials. Control mice without $CCl_4$ received vehicle (10% Tween-20) only. Serum ALT was determined at T24.

As seen in Table 5 below, dose correlated reduction in serum ALT levels were observed almost for all the extracts. The highest reductions in serum ALT levels were observed for mice treated with 400 mg/kg of *Artemisia capillaris* (R0594) (48.0%) followed by 300 mg/kg of the same plant material (29.9%). These reductions were statistically significant. At 400 mg/kg, both *Agrimonia* and Loesyn showed very similar level of reduction in ALT level (i.e. 28%) with P-values of 0.07 and 0.04, respectively. There was a 100% survival rate for all the groups including vehicle treated $CCl_4$ control. At lease in this batch *Artemisia capillaris* (R0594) showed superiority in inhibition of serum ALT level than any of the other hits tested.

TABLE 5

Dose-study using $CCl_4$ induced hepatotoxicity model summary

| Group | N | Material | Code | Part | Dose (mg/kg) | $CCl_4$ (μl/kg) | % Change | P-values |
|---|---|---|---|---|---|---|---|---|
| G-1 | 5 | Control (−) | — | — | 0 | 0 | — | — |
| G-2 | 10 | Carbon tetrachloride | $CCl_4$ | — | 0 | 25 | — | — |
| G-3 | 10 | *Agrimonia eupatoria* | E1399 | — | 400 | 25 | 28.2 | 0.07 |
| G-4 | 10 | *Agrimonia eupatoria* | E1399 | — | 300 | 25 | 19.5 | 0.18 |
| G-5 | 10 | *Agrimonia eupatoria* | E1399 | — | 200 | 25 | 20.5 | 0.28 |
| G-6 | 10 | N931 (2% alosin) | QMA2 | — | 400 | 25 | 28.6 | 0.04 |
| G-7 | 10 | N931 (2% alosin) | QMA2 | — | 300 | 25 | 22.0 | 0.16 |
| G-8 | 10 | N931 (2% alosin) | QMA2 | — | 200 | 25 | 12.8 | 0.54 |
| G-9 | 10 | *Artemisia capillaris* | R0594 | Whole | 400 | 25 | 48.0 | 0.002 |
| G-10 | 10 | *Artemisia capillaris* | R0594 | Whole | 300 | 25 | 29.9 | 0.06 |
| G-11 | 10 | *Schisandra chinensis* | L0498 | Fruit | 400 | 25 | 24.1 | 0.15 |
| G-12 | 10 | *Schisandra chinensis* | L0498 | Fruit | 300 | 25 | 17.7 | 0.22 |

TABLE 6

Summary of solvent extraction of dried ground aerial parts of *Artemisia capillaris*

| Sample Code | Extraction Solvent | Extraction Yield (%) |
|---|---|---|
| R684-100EE | 100% EtOH | 11.7 |
| R684-70EE | 70% EtOH | 19.2 |
| R684-50EE | 50% EtOH | 22.5 |

Example 7

Preparation of Organic Extracts of *Artemisia Capillaris*

Dried ground aerial parts *Artemisia capillaris* (2.5 kg) were cut, crushed, and then extracted with approximately 15-fold volume (37.5 L) of 70% ethyl alcohol in water (v/v). The extraction was carried out at 85° C. for 3 hrs. After filtration, the ethanol solution was concentrated by rotatory evaporator under vacuum at 40° C. This extraction and concentration procedure was repeated two times with 10 fold volume (25 L) of 70% ethyl alcohol in water (v/v) for 2 hrs. The concentrated extract solution was evaporated to dryness by vacuum dry oven to give 480 g of *Artemisia capillaris* 70% EtOH extract powder (lot #RN367-3-60M) with extraction yield 19.2%.

Dried ground *Artemisia capillaris* herb (180.4) g was extracted with 70% ethanol in water three times by refluxing one hour each time. The organic solution was combined and evaporated under vacuum to provide 70% ethanol extract (R594-70EE) 37.7 g with a yield of 20.9%. Similar results were obtained using the same procedure, but with the organic solvent being replaced with methanol or ethanol to provide a methanol extract (ME) or ethanol extract (EE), Ethanol:$H_2O$ (7:3) extracts, Ethanol:$H_2O$ (1:1) extracts, Ethanol:$H_2O$ (3:7) extracts and water extracts respectively. The solvent extraction process is summarized in Table 6.

TABLE 6-continued

Summary of solvent extraction of dried ground aerial parts of *Artemisia capillaris*

| Sample Code | Extraction Solvent | Extraction Yield (%) |
|---|---|---|
| R684-30EE | 30% EtOH | 22.9 |
| R684-W | Water | 25.7 |
| R594-70EE | 70% EtOH | 20.9 |
| RN425-6-70EE | 70% EtOH | 17.9 |
| RN425-7-70EE | 70% EtOH | 18 |
| RN425-8-70EE | 70% EtOH | 17.4 |
| RN425-11-70EE | 70% EtOH | 19.2 |
| RN425-12-70EE | 70% EtOH | 19.2 |
| RN425-13-70EE | 70% EtOH | 19.2 |
| RN425-14-70EE | 70% EtOH | 19.1 |

Example 8

Bioassay-Guided Fractionation of *Artemisia Capillaris* Extracts

The *Artemisia capillaris* 70% ethanol extract (RN425-7-70EE, 20 g) was partitioned between hexanes (200 mL) and water (250 mL) for three times. The combined hexanes solution was freed from solvent by vacuum to give hexanes extract (HE) 1.43 g. The aqueous layer was extracted with ethyl acetate (200 mL) for three times. The combined ethyl acetate layers were dried out in vacuum to give the ethyl acetate extract (EA) 2.29 g. The aqueous layer was further extracted with butanol (200 mL) for three times to give butanol extract (BU) 3.70 g. The remaining aqueous layer was freeze-dried to give aqueous extract (WA) 15.3 g. The 70% EE and HE, EA, BU and WA were tested for in $CCl_4$ induced hepatotoxicity model in mice. HE, EA, BU were inactive, while 70% EE showed 25.27% ALT inhibition at 400 mg/kg and WA fraction showed 37.49% inhibition at 300 mg/kg level with P≤0.05.

The active fraction WA was further fractionated by HP20SS chromatography. WA (4.4 g) was dissolved in 20% EtOH in water and loaded to one HP20SS (Diaion, Mitsubishi Chemical Corporation, Japan, 160 g) column pre-conditioned with 20% EtOH in water. The column was eluted with 800 mL 20% EtOH in water, 600 mL 40% EtOH in water, 400 mL 60% EtOH, 200 mL 80% EtOH, and finally washed with 200 mL EtOH and 200 mL acetone. Two major fractions HP-01 (3.67 g, 83.4%) and HP-02 (305.7 mg, 6.95%) were collected and tested in the $CCl_4$ induced hepatotoxicity mice model. The major components of HP-01 are oligosaccharides and polysaccharides. HP-02 contains mainly polyphenols. HP-01 demonstrated similar ALT inhibition compared to WA with 32.86% inhibition at 300 mg/kg. HP-02 is inactive in the same model indicating polyphenol is not contributing to the activity of this plant.

The active fraction HP-01 was further fractionated by a LH-20 open column. HP-01 (1.06 g) was dissolved in water and loaded to one LH-20 column preconditioned in water and with a gradient elution by MeOH/H2O to give 4 fractions, LH-01 (43.4 mg, 4.26%), LH-02 (799.6 mg, 78.5%), Chlorogenic acid (LH-03, 45.4 mg, 4.5%) and LH-04 (23.1 mg, 2.27%). Only the major fraction LH-02 was tested in the in vivo study due to the sample limitations. LH-02, 78.5% of HP-01, didn't show any efficacy in the $CCl_4$ induced animal model at 300 mg/kg level. Chlorogenic acid (C3878, Sigma-Aldrich, USA), a constituent of HP-01 with a ratio of about 4.5%, didn't show any inhibition when tested at 200 mg/kg level. The in vivo data of the present study clearly demonstrated that water soluble components, other than chlorogenic acid and polyphenols, are responsible for the hepatoprotective activity of *Artemisia* extract. The active polysaccharides content is less than 10% of the WA fraction. This information is summarized in Table 7.

TABLE 7

Hepatoprotective efficacy of fractions and compounds of R684-70EE

| Sample code | Dose (mg/kg) | CCl4 Dosage | % Change of ALT | p values |
|---|---|---|---|---|
| R684-70EE | 400 | 25 | 25.27 | 0.040 |
| R684-HE | 300 | 25 | −2.26 | 0.864 |
| R684-EA | 300 | 25 | 13.78 | 0.359 |
| R684-BU | 300 | 25 | 14.96 | 0.219 |
| R684-WA | 300 | 25 | 37.49 | 0.003 |
| HP-01 | 300 | 25 | 32.86 | 0.054 |
| HP-02 | 300 | 25 | −10.03 | 0.537 |
| LH-02 | 300 | 25 | −0.73 | 0.961 |
| Chlorogenic acid | 200 | 25 | −24.14 | 0.192 |

Example 9

Fraction Separation of Active HP-1 Sample by Membrane Dialysis

The liver protective fraction—HP-01 as shown in Example 8 and Table 7 from *Artemisia capillaris* was dissolved in appropriate volume of distilled water and dialyzed in the dialysis membrane tubes against distilled water (cut-off MW 2000) for 3 h each time and for 3 times. Both the retained and combined dialyzed solutions were freezing-dried to give two samples DA-1 (MW>2000, 13.79%) and DA-2 (MW<2000, 84.54%). DA-2 was further dialyzed with molecular weight cutoff at 500 following the same procedure as the previous dialysis. DA-3 (500<MW<2000, 16.7%) and DA-4 (MW<500, 79.7%) were collected. DA-1, DA-3, and DA-4 were tested in the $CCl_4$ induced mice model. DA-1 with molecular weight above 2000 showed the highest inhibition in serum ALT level with statistical significance compared with DA-3 and DA-4. Molecular weight under 500 didn't show any efficacy in this in vivo model. This information is summarized in Table 8.

TABLE 8

Hepatoprotective efficacy of dialysis samples of HP-01

| Sample code | Molecular Weight | Content % | Dose (mg/kg) | CCl4 Dosage | % Reduction of ALT | p values |
|---|---|---|---|---|---|---|
| DA-1 | MW > 2000 | 13.79% | 300 | 25 | 47.47 | 0.04 |
| DA-3 | 500 < MW < 2000 | 16.7% | 300 | 25 | 39.19 | 0.09 |
| DA-4 | MW < 500 | 79.7% | 300 | 25 | −14.14 | 0.441 |

Example 10

HPLC Analysis and Quantification of *Artemisia Capillaris* Extracts

The marker compounds chlorogenic acid (1, C3878, Sigma-Aldrich, USA), and dicaffeoyl acids (2-3) in the *Artemisia capillaris* extracts were identified based on LCMS analysis and literature reports and quantified with a C18 reversed-phase column (Phenomenex, Luna C18, 10 μm, 250 mm×4.6 mm) in a Hitachi HPLC system with UV wavelength 320 nm. The column was eluted with a binary gradient of 0.1% trifluoroacetic acid (TFA) in water and acetonitrile at 1 mL/min flow rate. The compounds 1-3 were quantified based on the reference compound chlorogenic acid. The chlorogenic acid content in 70% EE of *Artemisia capillaris* collected from different sources varied in a range of 1.5-4.8% (w/w) based on the calculation of peak area. This information is summarized in Tables 9-10.

TABLE 9

HPLC gradient table of Artemisia analysis

| Time (min) | 0.1% TFA/H₂O (%) | ACN (%) |
|---|---|---|
| 0 | 90 | 10 |
| 5 | 90 | 10 |
| 15 | 80 | 20 |
| 30 | 60 | 40 |
| 31 | 0 | 100 |
| 34 | 0 | 100 |
| 34.1 | 90 | 10 |
| 40 | 90 | 10 |

TABLE 10

Chlorogenic acids * content in *Artemisia capillaris* 70% ethanol extract

| Sample ID | 1 (%) | 2 (%) | 3 (%) | Total 1-3 (%) |
|---|---|---|---|---|
| R684-70EE | 4.72% | 3.57% | 2.35% | 10.63% |
| R594-70EE | 1.56% | 1.51% | 0.72% | 3.80% |
| L0523 | 3.12% | 1.48% | 1.73% | 6.33% |
| Honsea | 2.31% | 2.60% | 3.32% | 8.23% |
| E1466 | 4.55% | 3.02% | 2.18% | 9.76% |
| E1453 | 1.83% | 1.17% | 1.13% | 4.13% |
| RN425-6-70EE | 4.17% | 2.33% | 2.07% | 8.56% |
| RN425-7-70EE | 3.97% | 2.60% | 2.34% | 8.91% |
| RN425-8-70EE | 3.90% | 2.57% | 2.26% | 8.73% |
| RN425-11-70EE | 3.14% | 3.30% | 2.10% | 8.54% |
| RN425-12-70EE | 5.05% | 3.56% | 2.52% | 11.12% |
| RN425-13-70EE | 3.60% | 3.49% | 2.02% | 9.11% |
| RN425-14-70EE | 4.79% | 4.12% | 2.08% | 11.00% |

* Chlorogenic acid was used as the standard compound for quantification of all three peaks (1-3)

Example 11

Catechin Quantification of *Artemisia Capillaris* Extracts

Catechins in water fraction (WA) of *Artemisia capillaris* extracts was quantified by HPLC method. A Hitachi HPLC/PDA system with a C18 reversed-phase column (Phenomenex, USA, Luna 5 um, 250 mm×4.6 mm) was used for the catechins detection and quantitation at a flow rate of 1.0 mL/min with column temperature at 35° C. at a UV wavelength of 275 nm. Epicatechin (E1753, Sigma-Aldrich, USA) was not detected in all *Artemisia* samples, and only low content catechin was detected and quantified based on the catechin standard (C1251, Sigma-Aldrich, USA). The catechin content in the WA fraction of the *Artemisia capillaris* extracts, in a range of 0.02-0.32%, is not relevant to the liver protection properties of *Artemisia* extracts based on our in vivo study results. This information is summarized in Tables 11-12.

TABLE 11

Gradient table of HPLC analytical method

| Time (min) | 0.1% H₃PO₄/H₂O (%) | ACN (%) |
|---|---|---|
| 0.0 | 85.0 | 15.0 |
| 7.0 | 85.0 | 15.0 |
| 12.0 | 10.0 | 90.0 |
| 16.5 | 10.0 | 90.0 |
| 16.6 | 85.0 | 15.0 |
| 24.0 | 85.0 | 15.0 |

TABLE 12

Catechin quantification in *Artemisia* extract

| Sample name | Catechin | Epicatechin |
|---|---|---|
| E1466-WA | 0.09% | ND |
| E1453-WA | 0.15% | ND |
| L523-WA | 0.32% | ND |
| R684-WA | 0.10% | ND |
| R594-WA | 0.02% | ND |

ND: not detected

Example 12

Separation of Polysaccharides by Membrane Dialysis

The rude polysaccharides of HP-01 from *Artemisia capillaris* was dissolved in appropriate volume of distilled water and dialyzed in the dialysis membrane tubes against distilled water (cut-off MW 2000) for 3 h each time and for 3 times. Both the retained and combined dialyzed solutions were freezing-dried to give two samples DA-1 (MW>2000, 13.79%) and DA-2 (MW<2000, 84.54%). Both samples were tested in the $CCl_4$ induced mice model.

Example 13

Polysaccharides Analysis and Quantification by Gel Permeation Chromatography

The active fraction WA of *Artemisia capillaris* extracts were also analyzed by gel-permeation chromatography, which is a well-established method for assessing molecular weight distribution of polysaccharides. *Artemisia capillaris* polysaccharides were analyzed with a PolySep-SEC-P5000 column (Phenomenex, OOH-3145KO column, 300 mm×7.8 mm) by a Hitachi HPLC system quipped with a refractive index detector. The mobile phase was 0.1 M NaCl at a flow rate of 0.7 mL/min for 25 min. 20 μL at a concentration of 10 mg/mL was injected for each sample. Polysaccharides were quantified in seven ranges divided to >2000, 2000-1000, 100-500, 500-200, 200-50, 50-10, <10 KDa based on six Dextran molecular weight standards (American polymer Standards). The molecular weight distribution for water fraction samples of different extracts was varied. The live protective activity is associated with higher molecular distribution. Although the total polysaccharides contents are similar, the weight distribution is quite different among the *Artemisia capillaris* samples. The higher content the larger polysaccharides are, the better efficacy was observed for the *Artemisia capillaris*. The molecular weight distribution is shown in Table 13.

TABLE 13

Molecular weight distribution of biopolymers in *Artemisia* extract

| | MW distribution (kDa) | | | | | | | |
|---|---|---|---|---|---|---|---|---|
| | >2000 | 2000-1000 | 1000-500 | 500-200 | 200-50 | 50-10 | <10 | PSD (%) |
| E1453-WA | 1.2 | 6.6 | 11.7 | 16.9 | 38.2 | 25.3 | 0 | 0.36 |
| L523-WA | 0 | 0 | 0 | 13 | 82.7 | 4.3 | 0 | 0.33 |
| E1466-WA | 60.9 | 14.2 | 14.6 | 10.2 | 0.1 | 0 | 0 | 0.30 |
| R594-WA | 0 | 0 | 0 | 0 | 0 | 0 | 0 | 0.31 |

Example 14

Liver Protection Activity of *Artemisia Capillaris* Fractions on $CCl_4$ Model $CCl_4$-induced hepatotoxicity model was utilized to evaluate liver protection activity of *Artemisia capillaris* fractions in hexane (HE), ethyl acetate (EA), butanol (BU) and water. Control mice received 10% Tween-20 only. Serum ALT was determined at T24. While *Artemisia* fractions were administered at a dose of 300 mg/kg, the start materials were administered at a dose of 400 mg/kg.

As seen in Table 14, the highest inhibition in serum ALT was observed for the mice treated with the water fraction of *Artemisia* at a dose of 300 mg/kg indicating the possibility of presence of active marker in this fraction. However, this does not exclude existence of other active markers in other fractions. The original material (R684) maintained its efficacy given at a dose of 400 mg/kg. There was a 100% survival rate for all the groups in this model.

TABLE 14

Activity of *Artemisia capillaris* fractions

| Group | N | Material | ID | Dose (mg/kg) | $CCl_4$ (µl/kg) | % ALT Change | P-values |
|---|---|---|---|---|---|---|---|
| G-1 | 5 | Control (−) | — | 0 | 0 | — | — |
| G-2 | 10 | $CCl_4$ | — | 0 | 25 | — | — |
| G-3 | 10 | R684-HE | RN425-7-HE | 300 | 25 | −2.3 | 0.864 |
| G-4 | 10 | R684-EA | RN425-7-EA | 300 | 25 | 13.8 | 0.359 |
| G-5 | 10 | R684-BU | RN425-7-BU | 300 | 25 | 15.0 | 0.219 |
| G-6 | 10 | R684-WA | RN425-7-WA | 300 | 25 | 37.5 | 0.003 |
| G-7 | 10 | R684 | R684 | 400 | 25 | 25.3 | 0.040 |

Example 15

Preparation of Organic Extracts from *Schisandra Chinensis* Fruit

A total of 20 g of dried fruit of *Schisandra chinensis* were loaded into two 100 ml stainless steel tube and extracted twice with an organic 70% EtOH in water using an ASE 300 automatic extractor at 80 degree and pressure 1500 psi. The extract solution was automatically filtered and collected. The combined solution was evaporated to dryness by rotary evaporator to give crude 70% EtOH extract (9.65 g, 49.5%).

Similar results were obtained using the same procedure, but with the organic solvent being replaced with methanol or ethanol to provide a methanol extract (ME) or ethanol extract (EE), ethanol:$H_2O$ (7:3) extracts, ethanol:$H_2O$ (1:1) extracts, ethanol:$H_2O$ (3:7) extracts and water extracts respectively.

*Schisandra chinensis* extracts were manufactured with extraction of dried fruit by 70% ethanol/30% water (v/v). The extract was further processed to give extract in power form (Lot #) with no less than 2% total Schisandrins, including schisandrin, schisantherin A, schisandrin A (deoxyschisandrin), and schisandrin B.

Example 16

HPLC Analysis and Quantification of *Schisandra Chinensis* Extracts

Four active marker compounds, schisandrin (lot #110857, National Institute for Food and Control, China), schisantherin A (lot #11529-200503, National Institute for Food and Control, China), schisandrin A (deoxyschisandrin, lot #110764-200107, National Institute for Food and Control, China), and schisandrin B (lot #110765-200508, National Institute for Food and Control, China) were identified in *Schisandra chinensis* extracts and confirmed with *Schisandra chinensis* reference standard material (lot #140217, National Institute for Food and Control, China).

Active marker compounds were quantified by HPLC using a C18 reversed-phase column (Phenomenex, Luna C18, 10 µm, 250 mm×4.6 mm) in a Hitachi HPLC system with UV wavelength 250 nm by comparing to the reference standard material. The column was eluted with water and acetonitrile at 1 mL/min flow rate. A gradient table for this Example is shown in Table 15. Each individual peak was identified and integrated, and then total content of four compounds including schisandrins, schisantherin A, schisandrin A and schisandrin B were calculated based on RSM and that information is shown in Table 16.

TABLE 15

HPLC mobile phase gradient table for *Schisandra chinensis* extracts quantification

| Time (min) | $H_2O$ (%) | ACN (%) |
|---|---|---|
| 0 | 40 | 60 |
| 10 | 20 | 80 |
| 25 | 0 | 100 |
| 30 | 0 | 100 |
| 30.1 | 40 | 60 |
| 35 | 40 | 60 |

TABLE 16

Schisandins content in *Schisandra chinensis* extracts

| Sample code | Schisandrin | schisantherin A | deoxyschisandrin | schisandrin B | total schisandrins |
|---|---|---|---|---|---|
| L531 | 0.03% | 0.87% | 0.07% | 0.04% | 1.01% |
| L0498 | 1.16% | 0.10% | 0.23% | 0.58% | 2.07% |
| L499 | 3.80% | 0.69% | 0.77% | 1.84% | 7.10% |

Example 17

HPLC Quantification of Organic Acids in *Schisandra* Fruit Extracts

The presence of malic acid, shikimic acid and citric acid in 70% EtOH extracts generated in-house from different collections have been confirmed and are set forth in the Table 17. The organic acids were quantitatively analyzed by HPLC using a Hypersil GOLD aQ column (4.6×250 mm, 5 µm), and under isocratic conditions for 20 minutes at 5° C. with 50 mM potassium dihydrogen phosphate (adjusted pH to 2.8 with $H_3PO_4$) as the mobile phase, and with the flow rate at 0.7 ml/min. The organic acids were detected using a UV detector at 205 nm and identified based on retention time by comparison with organic acids standards.

TABLE 17

HPLC quantification of Organic Acids Content in Extracts of *Schisandra chinensis*

| Extracts | % Malic acid | % Shikimic acid | % Citric acid | Total % Organic acid |
|---|---|---|---|---|
| R768-70E-Fruit | 8.2% | 3.2% | 22.5% | 33.8% |
| R685-70E-Fruit | 15.5% | 2.9% | 26.5% | 44.9% |
| R767-70E-Fruit | 10.6% | 3.5% | 32.4% | 46.5% |
| R597-70E-Fruit | 14.4% | 3.3% | 18.8% | 36.6% |
| R768-70E-Meat | 9.1% | 2.4% | 20.6% | 32.2% |
| R768-70E-Seed | 4.9% | 1.3% | 8.5% | 14.7% |
| R685-70E-Seed | 7.7% | 1.3% | 10.8% | 19.9% |
| R766-70E-Seed | 0.8% | 0.0% | 1.3% | 2.1% |
| L498 | 0.1% | 0.8% | 0.0% | 0.8% |
| L499 | 0.3% | 0.5% | 0.0% | 0.8% |
| E1467 | 0.0% | 0.1% | 0.0% | 0.1% |
| E1469 | 0.0% | 0.2% | 0.0% | 0.2% |
| L529 | 0.0% | 0.2% | 0.0% | 0.2% |

Example 18

*Artemisia* and *Schisandra* Extracts in Different Combinations for Liver Protection in APAP and $CCl_4$ Models Once the lead plants such as *Artemisia capillaries* and *Schisandra chinensis* were selected, their efficacy in liver protection were assessed at different combination ratios at 4:1, 2:1, 1:1, 1:2 and 1:4 in APAP and $CCl_4$ induced hepatotoxicity models. The two plant combinations were coded as "SA" using the first letter of each plant, i.e. "S" for *Schisandra chinensis* and "A" for *Artemisia capillaries*. As seen in the Table 18 below, while all blends showed some sort of liver protection, the highest protection with statistically significant, 48.0% reductions as measured in serum ALT level were observed when mice were treated with a blend of *Schizandra* and *Artemisia* at a ratio of 2:1 with a total dose of 400 mg/kg. Similarly, in the $CCl_4$ model, the highest liver protection with statistically significant, 40.6% reductions as measured in serum ALT level were observed when mice were treated with a blend of *Schizandra* and *Artemisia* at a ratio of 1:2 with a total dose of 400 mg/kg. There was a 100% survival rate for this specific ratio in both models.

TABLE 18

Efficacy of composition SA in APAP/$CCl_4$-induced hepatotoxicity model

| Group | N | Material | Ratio | Dose (mg/kg) S-R0498:A-R0684 | APAP Dose (mg/kg) | APAP % Change | APAP P-values | $CCl_4$ Dose (mg/kg) | $CCl_4$ % Change | $CCl_4$ P-values |
|---|---|---|---|---|---|---|---|---|---|---|
| G-1 | 5 | Control (−) | — | 0 | 0 | — | — | 0 | — | — |
| G-2 | 10 | APAP/CCL4 | — | 0 | 400 | — | — | 25 | — | — |
| G-3 | 10 | Composition #SA1 | 4:1 | 320:80 | 400 | 23.1 | 0.32 | 25 | 8.8 | 0.46 |
| G-4 | 10 | Composition #SA2 | 2:1 | 266.7:133.3 | 400 | 48.0 | 0.01 | 25 | 4.4 | 0.74 |
| G-5 | 10 | Composition #SA3 | 1:1 | 200:200 | 400 | 24.4 | 0.27 | 25 | 17.8 | 0.13 |
| G-6 | 10 | Composition #SA4 | 1:2 | 133.3:266.7 | 400 | 13.1 | 0.58 | 25 | 40.6 | 0.0003 |
| G-7 | 10 | Composition #SA5 | 1:4 | 80:320 | 400 | 23.7 | 0.49 | 25 | 11.5 | 0.33 |

The highest efficacy in liver protection were observed when *Schisandra* and *Artemisia* were blended in a 2S:1A (APAP model) and 1S:2A (CCl₄ model). As a result, these ratios were considered as hits.

Example 19

Preparation of Combination SAL Composition

A contemplated SAL Combination composition (lot #RN425-1501) was produced by blending of 320 g of *Schisandra* extract (lot #E1458), 263 g of *Artemisia* extract (lot #RN425-13), 377 g of *Artemisia* extract (lot #RN425-14) and 240 g of N931(E1459 2% Aloesin) with Ribbon blender (Hankook P. M. EMG, Korea) at 30 rpm for 1 h to give 1.17 kg of SAL combination (lot #RN425-1501) at a ratio of *Schisandra:Artemisia*: N931=4:8:3 by weight.

Example 20

Evaluation of Liver Protection Activity of Blends of *Schisandra Chinensis, Artemisia Capillaris* and N931 in APAP/CCl₄ Models Two of the lead blend ratios of *Schisandra chinensis* and *Artemisia capillaries* at 2S:1A (APAP model) and 1S:2A (CCl₄ model) were selected for further liver protection activity by adding a third lead component (Loesyn) and designated as SAL. "L" stands for the Loesyn. N931 was added at 10, 20 and 30% ratio by weight to the 2S:1A combination and at 10, 20 and 25% ratio by weight to the 1S:2A combinations. This composition was tested in APAP/CCl₄-induced hepatotoxicity model. Mice were treated with the composition SAL at a dose of 400 mg/kg. While all the compositions at a different ratio showed a certain degree of liver protection, as seen in Table 19, the highest reductions in serum ALT (51.9%, P=0.01) and hence highest protection was observed when mice were treated with SAL at a dose of 400 mg/kg in a ratio of 106.7/213.3/80, respectively. There was a 100% survival rate for this specific ratio in this model.

Similarly, While all the compositions at a different ratio showed a certain degree of liver protection, as seen in table 19, the highest reductions in serum ALT (42.3%, P=0.01) was observed when mice were treated with SAL at a dose of 400 mg/kg in a ratio of 106.7/213.3/80, respectively. There was a 100% survival rate for this specific ratio in this model.

While multiple compositions showed efficacy in protecting the liver, the highest protection were observed when 20% of Loesyn by weight was added in a 1S:2A ratio in both models yielding a final 4S:8A:3L ratio for the composition SAL. As a result, this ratio, 4S:8A:3L, was considered as the lead composition.

Example 21

Dose-Response Effect of Composition Comprising *Schisandra Chinensis, Artemisia Capillaris* and N931 in APAP and CCl₄-Induced Hepatotoxicity Model The optimum dosage of the composition SAL that would incur significant liver protection was evaluated both in APAP and CCl₄ induced models. Mice were gavaged orally the composition SAL at doses of 400 mg/kg, 325 mg/kg and 250 mg/kg suspended in 10% Tween-20. The vehicle control group received the carrier solution only. As seen in Table 20, in the APAP group, dose-correlated inhibitions in serum ALT were observed for the composition. 52.5% (p=0.001), 48.5% (p=0.012) and 34.6% (p=0.079) inhibitions were observed for mice treated with doses of 400 mg/kg, 325 mg/kg and 250 mg/kg SAL, respectively. Similarly, in the CCl₄ group, dose-correlated inhibitions in serum ALT were observed for the composition. 46.3% (p=0.003), 39.5% (p=0.007) and 29.9% (p=0.036) inhibitions were observed for mice treated with doses of 400 mg/kg, 325 mg/kg and 250 mg/kg SAL, respectively. There was a 100% survival rate for all the groups in both models. The composition SAL has provided statistically significant (CCL4) protection in liver damage at a dosage level as low as 250 mg/kg at 1S:2A with a 20% L.

Here we tested the efficacy of individual plants such as *Schisandra, Artemisia* and Loesyn at a dosage equivalent to each plant ratio in the compassion SAL as they appear in 4S:8A:3L at the highest dose tested (400 mg/kg). As seen in the Table 20, an average of 20% inhibition with 70-80% survival rates was observed for these plants at the given dose.

TABLE 19

Efficacy of composition SAL in APAP/CCl₄-induced hepatotoxicity model

| Group | N | Material | Ratio | Dose (mg/kg) L498/R684/N931 | Dose (mg/kg) | % Change | P-values | Dose (mg/kg) | % Change | P-values |
|---|---|---|---|---|---|---|---|---|---|---|
| G-1 | 5 | Control (−) | | 0 | 0 | — | — | 0 | — | — |
| G-2 | 10 | APAP/CCl₄ | | 0 | 400 | — | — | 25 | — | — |
| G-3 | 10 | Composition #SAL1 | (2:1) 10% | 186.7/93.3/120 | 400 | 23.3 | 0.12 | 25 | 26.1 | 0.09 |
| G-4 | 10 | Composition #SAL2 | (1:2) 25% | 213.3/106.7/80 | 400 | 19.2 | 0.48 | 25 | 17.2 | 0.27 |
| G-5 | 10 | Composition #SAL3 | (1:2) 20% | 240/120/40 | 400 | 44.8 | 0.02 | 25 | 37.8 | 0.05 |
| G-6 | 10 | Composition #SAL4 | (1:2) 10% | 100/200/100 | 400 | 42.6 | 0.06 | 25 | 28.1 | 0.10 |
| G-7 | 10 | Composition #SAL5 | (2:1) 30% | 106.7/213.3/80 | 400 | 51.9 | 0.01 | 25 | 42.3 | 0.01 |
| G-8 | 10 | Composition #SAL6 | (2:1) 20% | 120/240/40 | 400 | 37.2 | 0.09 | 25 | 38.7 | 0.02 |

TABLE 20

Dose-correlated liver protection of the composition SAL in APAP/CCl$_4$-induced hepatotoxicity model

| Group | N | Material | Dose/code | Dose (mg/kg) L498/R684/N931 | Dose (mg/kg) | % Change | P-values | Dose (mg/kg) | % Change | P-values |
|---|---|---|---|---|---|---|---|---|---|---|
| G-1 | 5 | Control (−) | — | 0 | 0 | — | — | 0 | — | — |
| G-2 | 10 | APAP/CCl$_4$ | — | 0 | 400 | — | — | 25 | — | — |
| G-3 | 10 | Composition | 400 | 106.7/213.3/80 | 400 | 52.5 | 0.001 | 25 | 46.3 | 0.003 |
| G-4 | 10 | #SAL5 | 325 | 86.7/173.3/65 | 400 | 48.5 | 0.012 | 25 | 39.5 | 0.007 |
| G-5 | 10 | (1:2) 20% | 250 | 66.7/133.3/50 | 400 | 34.6 | 0.079 | 25 | 29.9 | 0.036 |
| G-6 | 10 | *Schizandra* | L498 | 106.7 | 400 | 18.4 | 0.280 | 25 | 17.5 | 0.210 |
| G-7 | 10 | *Artemisia* | R684 | 213.3 | 400 | 20.8 | 0.466 | 25 | 22.8 | 0.110 |

Example 22

Evaluations of Synergy for the Composition SAL

Colby's equation (Colby, 1967) was utilized to evaluate the benefit of combining *Schizandra chinensis*, *Artemisia capillaris* and N931 in both APAP and CCL4 model. As seen in the Table 21 below, the observed values were greater than the expected hypothetical values (A+B−C) in both the model indicating the existence of synergy in formulating three ingredients at a specific ratio to result in SAL. The merit of blending *Schizandra*, *Artemisia* and N931 was confirmed by their synergistic protection of liver damage caused by APAP and CCl$_4$.

Example 23

Liver Protection Activity of the SAL Composition Against its Individual Components at a Dose of 300 mg/kg Both APAP and CCl$_4$ induced liver toxicity models were utilized to compare the liver protection activity of the composition SAL against its individual components at a dose of 300 mg/kg using reduced serum ALT level as a measure of efficacy. 10% Tween-20 was used as a carrier vehicle for all the materials. Control mice received Tween-20 only. Besides serum ALT, liver panel such as T. protein, T. bilirubin, albumin, AST, and bile acid were measured for control, APAP/CCl$_4$, SAL, at T24.

TABLE 22

Serum ALT level of the composition SAL and individual components in APAP and CCl$_4$ induced hepatotoxicity models at a dose of 300 mg/kg

| | ALT | | | | | | | | | | | |
|---|---|---|---|---|---|---|---|---|---|---|---|---|
| | APAP Model | | | | | | CCl$_4$ Model | | | | | |
| Stat. | Control | APAP | SAL | S | A | L | Control | CCL4 | SAL | S | A | L |
| Mean | 28.3 | 8052.0 | 4256.7 | 4651.7 | 4671.0 | 6715.6 | 22.0 | 10145.3 | 6393.1 | 6737.6 | 7361.7 | 6678.1 |
| SD | 4.5 | 1208.8 | 3917.9 | 1386.7 | 1967.9 | 3114.7 | 3.7 | 3121.8 | 3426.3 | 3751.8 | 1384.6 | 3295.5 |
| P-values | — | — | 0.05 | 0.001 | 0.01 | 0.38 | — | — | 0.04 | 0.07 | 0.03 | 0.05 |
| % | — | — | 47.1 | 42.2 | 42.0 | 16.6 | — | — | 37.0 | 33.6 | 27.4 | 34.2 |
| Survival rate (%) | 100 | 60 | 90 | 70 | 50 | 70 | 100 | 100 | 100 | 100 | 100 | 100 |

TABLE 21

Unexpected synergistic activity of *Schizandra chinensis*, *Artemisia capillaris* and N931 in liver protection.

| | SAL | | |
|---|---|---|---|
| Dose (mg/kg) | | APAP | CCL4 |
| 106.7 | *Schizandra* (S) | 18.4 | 17.5 |
| 213.3 | *Artemisia* (A) | 20.8 | 22.8 |
| 80.0 | N931 (L) | 20.8 | 15.0 |
| | (x + y + Z) = A | 60.0 | 55.3 |
| | (xyz)/10000 = B | 0.8 | 0.6 |
| | ((xy) + (xz) + (yz))/100 = C | 12.0 | 10.0 |
| 400 | Expected (SAL) | 48.8 | 45.9 |
| | Observed (SAL) | 52.8 | 46.3 |

As seen in Tables 23 and 24, AST as a measure of efficacy, the composition (SAL) showed enhanced liver damage protection than vehicle in the APAP model (i.e. 60.6%). Statistically significant 47.1, 42.2, 42.0, and 16.6% reductions in serum ALT were observed for mice treated with SAL, S (*Schisandra*), A (*Artemisia*) and L (N931) compared to vehicle group, respectively. The lowest survival rate (50%) was observed for mice treated with *Artemisia*.

Substantiating the APAP model, the composition SAL showed greater liver protection than each individual component at a dose of 300 mg/kg in the CCl$_4$ model using serum ALT as a measure of efficacy. In addition, using AST as a measure of efficacy, the composition (SAL) showed enhanced damage protection than vehicle (i.e. 32.5%). There was a 100% survival rate for all the groups in this model.

TABLE 23

Liver panel markers compared to vehicle treated mice in APAP model

| | APAP | | | | |
|---|---|---|---|---|---|
| Group | AST | Bile Acid | T. bilirubin | Albumin | T. Protein |
| Control | 77.7 ± 28.3 | 1.0 ± 0.0 | 0.1 ± 0.0 | 2.67 ± 0.09 | 4.70 ± 0.24 |
| Vehicle | 4707.7 ± 2899.1 | 76.2 ± 24.8 | 0.5 ± 0.2 | 2.33 ± 0.20 | 4.43 ± 0.22 |
| SAL | 1855.7 ± 1859.6* | 15.1 ± 5.7* | 0.3 ± 0.1* | 2.71 ± 0.12* | 4.84 ± 0.12* |

As shown in Table 24, the composition SAL showed improved liver associated biomarkers such as bile acid, T. bilirubin and T. protein in APAP model compared when compared to vehicle treated APAP positive mice. Similarly, statistically significant bile acid clearance was observed for mice treated with the composition SAL in $CCl_4$ model when compared to vehicle group.

TABLE 24

Liver panel markers compared to vehicle treated mice in $CCl_4$ model.

| | $CCl_4$ | | | | |
|---|---|---|---|---|---|
| Group | AST | Bile Acid | T. bilirubin | Albumin | T. Protein |
| Control | 68.0 ± 17.9 | 1.0 ± 1.0 | 0.2 ± 0.1 | 2.7 ± 0.2 | 4.9 ± 0.4 |
| Vehicle | 4570.9 ± 1121.3 | 22.1 ± 7.1 | 0.4 ± 0.1 | 2.7 ± 0.1 | 4.9 ± 0.2 |
| SAL | 3085.4 ± 1635.3* | 14.8 ± 7.2* | 0.3 ± 0.1 | 2.7 ± 0.1 | 4.8 ± 0.2 |

Example 24

Efficacy Confirmation Study of the Composition SAL in APAP and CCL4-Induced Hepatotoxicity Models Documenting the superiority in liver protection activity of composition SAL, a confirmatory study was carried out using both APAP and $CCl_4$ induced hepatotoxicity model. Mice were gavaged with the composition SAL at 400 mg/kg orally. 10% Tween-20 was used as a carrier vehicle for all the materials. Control mice received Tween-20 only. Besides serum ALT, Liver panel such as T. protein, total bilirubin, direct and indirect bilirubin, albumin, globulin, AST, bile acid and ALP were measured for control, APAP/$CCl_4$, SAL, at T24.

As seen in Tables 25 and 26 below, statistically significant inhibitions in serum ALT, AST, conjugated bilirubin and bile acid were observed for mice treated with the composition SAL. These inhibitions were 34.0%, 44.5%, 60.0% and 26.7% reductions from the vehicle treated group. Similarly, the composition SAL showed statistically significant reductions in serum ALT level (44.0% reductions) and a strong trend in reduction in AST (35.9% reductions) compared to vehicle treated mice. Overall, the composition SAL provided greater protection to liver damage in multiple frequently used animal models, which is shown in Table 27.

TABLE 25

Summary of Liver panel analyte levels for mice treated with SAL, in APAP induced hepatotoxicity model.

| Analyte | Control | APAP (400 mg/kg) | SAL (400 mg/kg) |
|---|---|---|---|
| ALT | 30.8 ± 4.9 | 10363.3 ± 4793.8 | 5808.8 ± 3189.7* |
| AST | 68.6 ± 32.0 | 4189.7 ± 2227.1 | 2684.8 ± 1565.2 |
| T. bilirubin | 0.15 ± 0.05 | 0.52 ± 0.16 | 0.43 ± 0.15 |

TABLE 25-continued

Summary of Liver panel analyte levels for mice treated with SAL, in APAP induced hepatotoxicity model.

| Analyte | Control | APAP (400 mg/kg) | SAL (400 mg/kg) |
|---|---|---|---|
| Direct | 0.00 ± 0.00 | 0.18 ± 0.08 | 0.11 ± 0.06 |
| Indirect bilirubin | 0.15 ± 0.05 | 0.33 ± 0.16 | 0.31 ± 0.12 |
| ALP | 91.9 ± 22.5 | 177.7 ± 33.4 | 145.4 ± 32.0 |
| Bile Acid | 1.2 ± 0.4 | 18.7 ± 8.5 | 18.5 ± 11.7 |
| T. Protein | 4.46 ± 0.20 | 4.53 ± 0.37 | 4.45 ± 0.54 |
| Albumin | 2.50 ± 0.12 | 2.60 ± 0.21 | 2.61 ± 0.31 |
| Globulin | 1.96 ± 0.08 | 1.93 ± 0.18 | 1.84 ± 0.26 |

TABLE 26

Summary of Liver panel analyte levels for mice treated with SAL, in $CCl_4$-induced hepatotoxicity model.

| Analyte | Control | $CCl_4$ (25 μ/kg) | SAL (400 mg/kg) |
|---|---|---|---|
| ALT | 20.0 ± 6.5 | 9796.5 ± 2223.4 | 6466.6 ± 2696.5* |
| AST | 69.9 ± 16.1 | 5031.8 ± 1510.2 | 2794.0 ± 1427.2* |
| T. bilirubin | 0.17 ± 0.05 | 0.40 ± 0.11 | 0.31 ± 0.09 |
| Direct bilirubin | 0.00 ± 0.00 | 0.11 ± 0.03 | 0.04 ± 0.05* |
| Indirect bilirubin | 0.17 ± 0.05 | 0.29 ± 0.09 | 0.27 ± 0.07 |
| ALP | 76.6 ± 15.7 | 139.7 ± 65.5 | 115.0 ± 19.5 |
| Bile Acid | 1.2 ± 0.4 | 30.1 ± 8.6 | 22.1 ± 7.4* |
| T. Protein | 4.50 ± 0.19 | 4.62 ± 0.20 | 4.61 ± 0.18 |
| Albumin | 2.42 ± 0.13 | 2.64 ± 0.07 | 2.60 ± 0.09 |
| Globulin | 2.08 ± 0.14 | 1.98 ± 0.15 | 2.01 ± 0.18 |

TABLE 27

Summary of percent changes of liver panel markers from SAL group compared to vehicle treated mice in APAP/CCl$_4$ models.

| Analyte | % Changes SAL (400 mg/kg) | |
| --- | --- | --- |
|  | APAP | CCl$_4$ |
| ALT | 43.95 | 33.99 |
| AST | 35.9 | 44.47 |
| T. bilirubin | 17.7 | 22.2 |
| Direct bilirubin | 38.64 | 60.00 |
| Indirect bilirubin | 6.25 | 7.69 |
| ALP | 18.2 | 17.7 |
| Bile Acid | 0.9 | 26.6 |
| T. Protein | 1.8 | 0.2 |
| Albumin | −0.48 | 1.68 |
| Globulin | 4.96 | −1.46 |

(+): ↓ Decrease from APAP/CCl$_4$ (+) vehicle
(−): ↑ Increase from APAP/CCl$_4$ (+) vehicle Example 25

Effect of Composition SAL on Oxidative Stress Biomarkers in Liver Homogenates Collected from CCl$_4$-Induced Hepatotoxicity Model Additional confirmatory assays were carried out to assess the effect of the composition SAL in protecting liver using CCl$_4$-induced hepatotoxicity model. Mice were gavaged with the composition SAL at 400 mg/kg orally. 10% tween 20 was used as a carrier vehicle. Control mice received tween 20 only. Liver tissues were collected immediately after necropsy and were kept in dry ice until transferred to −80° C. Material were then shipped to a contract laboratory (Brunswick Laboratories, 200 Turnpike Rd, MA 01772, USA) in dry ice for final specimen processing and biomarker analysis. Hepatic Glutathione (GSH) and Superoxide dismutases (SODs) were evaluated.

Glutathione (GSH) is a key intracellular tripeptide thiol that helps protecting cells from free radical damage by providing reducing equivalents for the reduction of lipid hydroperoxides. During this process, oxidized glutathione (GSSG) forms as a reaction product. GSH level has been used as indicative biomarkers of in vivo oxidant and oxidative stress level in cells and tissues. In this analysis, the sulfhydryl group of GSH reacts with DTNB (5,5'-dithio-bis-2-(nitrobenzoic acid)) to produce a produces a yellow colored 5-thio-2-nitrobenzoic acid (TNB) product. The amount of GSH in the biological samples is determined via measurement of the absorbance of TNB at 410 nm.

Superoxide dismutases (SODs) are metallo-enzymes that catalyze the dismutation of the superoxide anion to molecular oxygen and hydrogen peroxide. SOD is considered one of the most important antioxidant enzymes in vivo. The SOD assay is a colorimetric assay, which utilizes a tetrazolium salt to measure the dismutation of superoxide radicals that were induced by xanthine oxidase and xanthine, and the activity of SOD in a given sample is quantified by the standard curve generated using the SOD standards. One unit of SOD is defined as the amount of enzyme needed to exhibit 50% dismutation of superoxide radicals.

As seen in the Table 28 below, taking the per gram of protein level of each biomarker tested, the composition SAL replenished the depleted hepatic glutathione in association with an increased in hepatic superoxide dismutase. These findings in conjunction with previously disclosed liver panel data, strongly suggest that the composition SAL possesses liver protection activity from oxidative stress elicited by CCL4-induced liver damage.

TABLE 28

Oxidative stress biomarkers levels using composition SAL treated mice liver homogenates

| Group | Dose (mg/kg) | N | GSH (nmole/mg of protein) | SOD (U/mg of protein) |
| --- | --- | --- | --- | --- |
| Control | 0 | 10 | 38.26 ± 9.52 | 19.04 ± 4.20 |
| CCl4 (25 µl/kg) | 0 | 9 | 57.87 ± 10.85 | 15.21 ± 6.09 |
| SAL | 400 | 9 | 72.91 ± 14.93* | 22.89 ± 7.95* |

*P ≤ 0.05

Example 26

Evaluation of Liver Protection Activity of Blends of *Astragalus Membranous, Schisandra Chinensis* and *Artemisia Capillaris* at Specific Ratios in CCl$_4$-Induced Hepatotoxicity Model Liver protection activity of combination comprised of two additional lead plant extracts were also evaluated in CCl$_4$ induced hepatotoxicity model in mice. *Astragalus membranous* was combined with *Schisandra chinensis* or *Artemisia capillaris* at 1:1, 1:2, 2:1, 1:4 and 4:1 ratios. As shown in Table 29, when *Astragalus* was blended with *Schisandra*, only one ratio i.e. 1:4 showed statistically non-significant (34.1%) reductions in serum ALT compared to vehicle treated injured mice. In contrast, higher magnitudes in liver protections were observed when *Astragalus* was combined with *Artemisia*. Statistically significant 46.3% and 57.7% inhibitions in serum ALT were observed for the 2:1 and 4:1 ratios of *Astragalus:Artemisia*, respectively. There was a 100% survival rate for all the ratios tested in this model.

TABLE 29

Data summary of mice serum ALT level in CCL4 - induced hepatotoxicity model treated by *Astragalus membranous*, *Schisandra chinensis* and *Artemisia capillaries* at specific ratios

| Group | N | Material | Ratio | Dose (mg/kg) or (µl/kg) | Mean | SD | % Change | P-values |
| --- | --- | --- | --- | --- | --- | --- | --- | --- |
| G-1 | 5 | Control (−) | — | 0 | 17.6 | 3.4 | — | — |
| G-2 | 10 | CCl$_4$ (µl/kg) | — | 25 | 9622.8 | 3945.1 | — | — |
| G-3 | 10 | *Astragalus:Schisandra* | 1:1 | 200:200 | 10921.5 | 3348.5 | −13.5 | 0.46 |
| G-4 | 10 |  | 1:2 | 133.3:266.7 | 10052.2 | 3146.6 | −4.5 | 0.80 |
| G-5 | 10 |  | 2:1 | 266.7:133.3 | 8707.3 | 2507.5 | 9.5 | 0.56 |
| G-6 | 10 |  | 1:4 | 80:320 | 6338.9 | 4398.4 | 34.1 | 0.11 |
| G-7 | 10 |  | 4:1 | 320:80 | 8483.8 | 4973.1 | 11.8 | 0.60 |

TABLE 29-continued

Data summary of mice serum ALT level in CCL4 - induced hepatotoxicity model treated by *Astragalus membranous*, *Schisandra chinensis* and *Artemisia capillaries* at specific ratios

| Group | N | Material | Ratio | Dose (mg/kg) or (μl/kg) | Mean | SD | % Change | P-values |
|---|---|---|---|---|---|---|---|---|
| G-8 | 10 | *Astragalus:Artemisia* | 1:1 | 200:200 | 7941.6 | 2080.4 | 17.5 | 0.27 |
| G-9 | 10 | | 1:2 | 133.3:266.7 | 9245.6 | 2523.2 | 3.9 | 0.81 |
| G-10 | 10 | | 2:1 | 266.7:133.3 | 5170.4 | 2005.0 | 46.3 | 0.007 |
| G-11 | 10 | | 1:4 | 80:320 | 6373.7 | 3580.6 | 33.8 | 0.08 |
| G-12 | 10 | | 4:1 | 320:80 | 4067.5 | 2483.2 | 57.7 | 0.002 |

Thus, specific embodiments and methods of compounds and compositions useful for liver health management, including stereoisomers, pharmaceutically or nutraceutically acceptable salts, tautomers, glycosides and prodrugs of the disclosed compounds, along with related methods of improving and maintaining liver health have been disclosed. It should be apparent, however, to those skilled in the art that many more modifications besides those already described are possible without departing from the inventive concepts herein. The inventive subject matter, therefore, is not to be restricted except in the spirit of the disclosure herein. Moreover, in interpreting the specification and claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

REFERENCES

Each of the below-listed references are the full citations of the references already disclosed herein. It should be noted that each of these references is incorporated herein by reference in its entirety.

1. Ajith T A, Hema U, Aswathy M S. *Zingiber officinale* Roscoe prevents acetaminophen-induced acute hepatotoxicity by enhancing hepatic antioxidant status. Food Chem. Toxicol. 2007; 45:2267-2272.
2. Albano E., Lott A. K., Slater T. F., Stier A., Symons M. C. R., and Tomasi A. (1982) Spin trapping studies on the free radical products formed by metabolic activation of carbon tetrachloride in rat liver microsomal fractions, isolated hepatocytes and in vivo. Biochem. J. 204:593-603.
3. Amat N, Upur H, Blažeković B. In vivo hepatoprotective activity of the aqueous extract of *Artemisia absinthium* L. against chemically and immunologically induced liver injuries in mice. J Ethnopharmacol. 2010; 131(2):478-84
4. An R B, Sohn D H, Kim Y C. Hepatoprotective compounds of the roots of *Cudrania tricuspidata* on tacrine-induced cytotoxicity in Hep G2 cells. Biol Pharm Bull. 2006; 29(4):838-40.
5. Bajt M L, Cover C, Lemasters J J, Jaeschke H. Nuclear translocation of endonuclease G and apoptosisinducing factor during acetaminophen-induced liver cell injury. Toxicol. Sci. 2006; 94:217-225.
6. Bajt M L, Farhood A, Lemasters J J, Jaeschke H. Mitochondrial bax translocation accelerates DNA fragmentation and cell necrosis in a murine model of acetaminophen hepatotoxicity. J. Pharmacol. Exp. Ther. 2008; 324:8-14.
7. Bajt M L, Ramachandran A, Yan H M, Lebofsky M, Farhood A, Lemasters J J, Jaeschke H. Apoptosisinducing factor modulates mitochondrial oxidant stress in acetaminophen hepatotoxicity. Toxicol. Sci. 2011; 122:598-605.
8. Cha J D, Moon S E, Kim H Y, Lee J C, Lee K Y. The essential oil isolated from *Artemisia Capillaris* prevents LPS-induced production of NO and PGE(2) by inhibiting MAPK-mediated pathways in RAW 264.7 macrophages. Immunol Invest. 2009; 38:483-97.
9. Chamulitrat W., Blazka M. E., Jordan S. J., Luster M. I., and Mason R. P. (1995) Tumor necrosis factor-alpha and nitric oxide production in endotoxin-primed rats administered carbon tetrachloride. Life Sci. 57:2273-2280.
10. Chamulitrat W., Jordan S. J., and Mason R. P. (1994) Nitric oxide production during endotoxic shock in carbon tetrachloride-treated rats. Mol. Pharmacol. 46:391-397.
11. Cheeseman K. H., Davies M. J., Emery S., Maddix S. P., and Slater T. F. (1987) Effects of alpha-tocopherol on carbon tetrachloride metabolism in rat liver microsomes. Free Radic. Res. Commun. 3:325-330.
12. Choi J H, Kim D W, Yun N, Choi J S, Islam M N, Kim Y S, et al. Protective effects of hyperoside against carbon tetrachloride-induced liver damage in mice. J Nat Prod. 2011; 74:1055-60.
13. Choi M K, Han J M, Kim H G, Lee J S, Lee J S, Wang J H, Son S W, Park H J, Son C G. Aqueous extract of *Artemisia capillaris* exerts hepatoprotective action in alcohol-pyrazole-fed rat model. J Ethnopharmacol. 2013; 147(3): 662-70
14. Chu C Y, Tseng T H, Hwang J M, Chou F P, Wang C J. Protective effects of capillaris in on tert-butylhydroperoxide-induced oxidative damage in rat primary hepatocytes. Arch Toxicol. 1999; 73:263-8.
15. Colby, S R. Calculating Synergistic and Antagonistic Responses of Herbicide combinations. Weeds, Vol. 15, No. 1 (Jan., 1967), pp. 20-22.
16. Cover C, Mansouri A, Knight T R, Bajt M L, Lemasters J J, Pessayre D, Jaeschke H. Peroxynitriteinduced mitochondrial and endonuclease-mediated nuclear DNA damage in acetaminophen hepatotoxicity. J. Pharmacol. Exp. Ther. 2005; 315:879-887.
17. Czaja M. J., Xu J., and Alt E. (1995) Prevention of carbon tetrachloride-induced rat liver injury by soluble tumor necrosis factor receptor. Gastroenterology 108: 1849-1854.
18. Davern T J 2nd, James L P, Hinson J A, Polson J, Larson A M, Fontana R J, Lalani E, Munoz S, Shakil A O, Lee W M, Acute Liver Failure Study Group. Measurement of serum acetaminophen-protein adducts in patients with acute liver failure. Gastroenterology. 2006; 130:687-694
19. Feng G, Wang X, You C, Cheng X, Han Z, Zong L, Zhou C, Zhang M. Antiproliferative potential of *Artemisia capillaris* polysaccharide against human nasopharyngeal carcinoma cells. Carbohydr Polym. 2013; 15; 92(2):1040-5.
20. Han K H, Jeon Y J, Athukorala Y, Choi K D, Kim C J, Cho J K, et al. A water extract of *Artemisia Capillaris* prevents 2,2'-azobis(2-amidinopropane) dihydrochloride-induced liver damage in rats. J Med Food. 2006; 9:342-7.
21. Hanawa N, Shinohara M, Saberi B, Gaarde W A, Han D, Kaplowitz N. Role of JNK translocation to mitochondria leading to inhibition of mitochondria bioenergetics in acetaminophen-induced liver injury. J. Biol. Chem. 2008; 283:13565-13577.
22. He C S, Yue H Y, Xu J, Xue F, Liu J, Li Y Y, Jing H E. Protective effects of capillary *Artemisia* polysaccharide on oxidative injury to the liver in rats with obstructive jaundice. Exp Ther Med. 2012; 4(4):645-648.
23. Hogade M G, Patil ks, Wadkar G H, Mathapati S S, Dhumal P. Hepatoprotective activity of *Morus alba* (Linn.) leaves extract against carbon tetrachloride induced hepatotoxicity in rats. African Journal of Pharmacy and Pharmacology 2010; Vol. 4(10), pp. 731-734,
24. Hong J H, Lee I S. Cytoprotective effect of *Artemisia Capillaris* fractions on oxidative stress-induced apoptosis in V79 cells. Biofactors. 2009; 35:380-8.
25. Hong S H, Seo S H, Lee J H, Choi B T. The aqueous extract from *Artemisia capillaris* Thunb. Inhibits lipopolysaccharide-induced inflammatory response through preventing NF-kappaB activation in human hepatoma cell line and rat liver. Int J Mol Med. 2004; 13(5):717-20.
26. Hu Y Q, Tan R X, Chu M Y, Zhou J. Apoptosis in human hepatoma cell line SMMC-7721 induced by water-soluble macromolecular components of *Artemisia capillaris* Thunberg. Jpn J Cancer Res. 2000; 91(1):113-7.
27. Hung H Y, S C. Recent Studies and Progression of Yin Chen Hao (茵陳蒿 Yīn Chén Hāo), a Long-term Used Traditional Chinese Medicine. J Tradit Complement Med. 2013; 3(1): 2-6.
28. Jaeschke H, McGill M R, Ramachandran A. Oxidant stress, mitochondria, and cell death mechanisms in drug-induced liver injury: lessons learned from acetaminophen hepatotoxicity. Drug Metab. Rev. 2012a; 44:88-106.
29. Jaeschke H, Williams C D, McGill M R, Xie Y, Ramachandran A. Models of drug-induced liver injury for evaluation of phytotherapeutics and other natural products. Food Chem Toxicol. 2013 May; 55:279-89.
30. Jaeschke H. Glutathione disulfide formation and oxidant stress during acetaminophen-induced hepatotoxicity in mice in vivo: the protective effect of allopurinol. J. Pharmacol. Exp. Ther. 1990; 255:935-941.
31. James L P, Letzig L, Simpson P M, Capparelli E, Roberts D W, Hinson J A, Davern T J, Lee W M. Pharmacokinetics of acetaminophen-protein adducts in adults with acetaminophen overdose and acute liver failure. Drug Metab. Dispos. 2009; 37:1779-1784.
32. Jollow D J, Mitchell J R, Potter W Z, Davis D C, Gillette J R, Brodie B B. Acetaminophen-induced hepatic necrosis. II. Role of covalent binding in vivo. J. Pharmacol. Exp. Ther. 1973; 187:195-202.
33. Jung H A, Park J J, Islam M N, Jin S E, Min B S, Lee J H, et al. Inhibitory activity of coumarins from *Artemisia Capillaris* against advanced glycation end product formation. Arch Pharm Res. 2012; 35:1021-35.
34. Kim D W, Cho H I, Kim K M, Kim S J, Choi J S, Kim Y S, et al. Isorhamnetin-3-O-galactoside protects against CCl4-Induced hepatic injury in mice. Biomol Ther. 2012; 20:406-12.
35. Kim E K, Kwon K B, Han M J, Song M Y, Lee J H, Lv N, et al. Inhibitory effect of *Artemisia Capillaris* extract on cytokine-induced nitric oxide formation and cytotoxicity of RINm5F cells. Int J Mol Med. 2007; 19:535-40.
36. Kim S W, Kim H W, Woo M H, Lee J H, Choi J S, Min B S. Quantitative determination of bioactive compounds in some *Artemisia capillaris* by high-performance liquid chromatography. Nat Prod Sci. 2010; 16(4):233-238
37. Kon K, Kim J S, Jaeschke H, Lemasters J J. Mitochondrial permeability transition in acetaminopheninduced necrosis and apoptosis of cultured mouse hepatocytes. Hepatology. 2004; 40:1170-1179.
38. Koo H N, Hong S H, Jeong H J, Lee E H, Kim N G, Choi S D, et al. Inhibitory effect of *Artemisia Capillaris* on ethanol-induced cytokines (TNF-$\alpha$, IL-1$\alpha$) secretion in Hep G2 cells. Immunopharmacol Immunotoxicol. 2002; 24:441-53.
39. Kwon O S, Choi J S, Islam M N, Kim Y S, Kim H P. Inhibition of 5-lipoxygenase and skin inflammation by the aerial parts of *Artemisia Capillaris* and its constituents. Arch Pharm Res. 2011; 34:1561-9.
40. Larson A M. Acetaminophen hepatotoxicity. Clin. Liver Dis. 2007; 11:525-548.
41. Lee H I, Seo K O, Yun K W, Kim M J, Lee M K. Comparative study of the hepatoprotective efficacy of *Artemisia iwayomogi* and *Artemisia capillaris* on ethanol-administered mice. J Food Sci. 2011; 76(9):T207-11
42. Loguidice A, Boelsterli U A. Acetaminophen overdose-induced liver injury in mice is mediated by peroxynitrite independently of the cyclophilin D-regulated permeability transition. Hepatology. 2011; 54:969-978.
43. Luckey S. W. and Petersen D. R. (2001) Activation of Kupffer cells during the course of carbon tetrachloride-induced liver injury and fibrosis in rats. Exp. Mol. Pathol. 71:226-240.
44. Masubuchi Y, Suda C, Horie T. Involvement of mitochondrial permeability transition in acetaminophen-induced liver injury in mice. J. Hepatol. 2005; 42:110-116.
45. McGill M R, Sharpe M R, Williams C D, Taha M, Curry S C, Jaeschke H. The mechanism underlying acetaminophen-induced hepatotoxicity in humans and mice involves mitochondrial damage and nuclear DNA fragmentation. J. Clin. Invest. 2012a; 122:1574-1583.
46. McGill M R, Williams C D, Xie Y, Ramachandran A, Jaeschke H. Acetaminophen-induced liver injury in rats and mice: Comparison of protein adducts, mitochondrial dysfunction, and oxidative stress in the mechanism of toxicity. Toxicol. Appl. Pharmacol. 2012b; 264:387-394.
47. Mitchell J R, Jollow D J, Potter W Z, Davis D C, Gillette J R, Brodie B B. Acetaminophen-induced hepatic necrosis. I. Role of drug metabolism. J. Pharmacol. Exp. Ther. 1973; 187:185-194.
48. Nakagawa H, Maeda S, Hikiba Y, Ohmae T, Shibata W, Yanai A, Sakamoto K, Ogura K, Noguchi T, Karin M, Ichijo H, Omata M. Deletion of apoptosis signal-regulating kinase 1 attenuates acetaminophen-induced liver injury by inhibiting c-Jun N-terminal kinase activation. Gastroenterology. 2008; 135:1311-21.
49. Nelson S. D. and Harrison P. J. (1987) Roles of cytochrome P450 in chemically induced cytotoxicity. In: Guengrich F. P. (Ed.), Mammalian Cytochromes P450, CRC Press, Boca Raton, pp. 19-80.

50. Panossian A, Wikman G. Pharmacology of *Schisandra chinensis* Bail.: an overview of Russian research and uses in medicine. J Ethnopharmacol. 2008; 118(2):183-212.
51. Park K M, Li Y, Kim B, Zhang H, Hwangbo K, Piao D G, Chi M J, Woo M H, Choi J S, Lee J H, Moon D C, Chang H W, Kim J R, Son J K. High-performance liquid chromatographic analysis for quantitation of marker compounds of *Artemisia capillaris* Thunb. Arch Pharm Res. 2012; 35(12):2153-2162
52. Poyer J. L., McCay P. B., Lai E. K., Janzen E. G., and Davis E. R. (1980) Confirmation of assignment of trichloromethyl radical spin adduct detected by spin trapping during 13C carbon tetrachloride metabolism in vitro and in vivo. Biochem. Biophys. Res. Commun. 94:1154-1160.
53. Qiu Y, Benet L Z, Burlingame A L. Identification of hepatic protein targets of the reactive metabolites of the non-hepatotoxic regioisomer of acetaminophen, 3'-hydroxyacetanilide, in the mouse in vivo using two-dimensional gel electrophoresis and mass spectrometry. Adv. Exp. Med. Biol. 2001; 500:663-673.
54. Ramachandran A, Lebofsky M, Baines C P, Lemasters J J, Jaeschke H. Cyclophilin D deficiency protects against acetaminophen-induced oxidant stress and liver injury. Free Radic. Res. 2011a; 45:156-164.
55. Renner H. (1985) The limited relevance of models used for testing human hepatic diseases and their prevention. In: Keppler E., Popper H., Bianchi L., and Reutter W. (Eds.), Mechanisms of Hepatocyte Injury and Death, MTP Press Ltd., Lancaster, pp. 311-320.
56. Reynolds E. S. (1963) Liver parenchymal cell injury. I. Initial alterations of the cell following poisoning with carbon tetrachloride. J. Cell Biol. 19:139-157.
57. Saito C, Lemasters J J, Jaeschke H. c-Jun N-terminal kinase modulates oxidant stress and peroxynitrite formation independent of inducible nitric oxide synthase in acetaminophen hepatotoxicity. Toxicol. Appl. Pharmacol. 2010a; 246:8-17.
58. Singab A N, Ayoub N A, Ali E N, Mostafa N M. Antioxidant and hepatoprotective activities of Egyptian moraceous plants against carbon tetrachloride-induced oxidative stress and liver damage in rats. Pharm Biol. 2010; 48(11):1255-64.
59. Slater T. F. (1981) Activation of carbon tetrachloride: chemical principles and biological significance. In: McBrien D. C. H., Slater T. F. (Eds.), Free Radicals, Lipid Peroxidation and Cancer, Academic Press, London, pp. 243-270.
60. Tien Y C, Liao J C, Chiu C S, Huang T H, Huang C Y, Chang W T, et al. Esculetin ameliorates carbon tetrachloride-mediated hepatic apoptosis in rats. Int J Mol Sci. 2011; 12:4053-67.
61. Tirmenstein M A, Nelson S D. Subcellular binding and effects on calcium homeostasis produced by acetaminophen and a nonhepatotoxic regioisomer, 3'-hydroxyacetanilide, in mouse liver. J. Biol. Chem. 1989; 264:9814-9819.
62. Wan Y, Wu Y L, Lian L H, Nan J X. Protective effect of *Ornithogalum saundersiae* Ait (Liliaceae) against acetaminophen-induced acute liver injury via CYP2E1 and HIF-1α. Chin. J. Nat. Med. 2012; 10:177-184.
63. Wang J H, Choi M K, Shin J W, Hwang S Y, Son C G. Antifibrotic effects of *Artemisia capillaris* and *Artemisia iwayomogi* in a carbon tetrachloride-induced chronic hepatic fibrosis animal model. J Ethnopharmacol. 2012; 140(1):179-85.
64. Weddle C C, Hornbrook K R, McCay P B. Lipid peroxidation and alteration of membrane lipids in isolated hepatocutes exposed to carbon tetrachloride. J. Biol. Chem. 1976; 251:4973-4978.
65. Yang C C, Fang J Y, Hong T L, Wang T C, Zhou Y E, Lin T C. Potential antioxidant properties and hepatoprotective effects of an aqueous extract formula derived from three Chinese medicinal herbs against CCl(4)-induced liver injury in rats. Int Immunopharmacol. 2013; 15(1):106-13.
66. Zaher H, Buters J T, Ward J M, Bruno M K, Lucas A M, Stern S T, Cohen S D, Gonzalez F J. Protection against acetaminophen toxicity in CYP1A2 and CYP2E1 double-null mice. Toxicol. Appl. Pharmacol. 1998; 152:193-199.
67. Zhao Y, Geng C A, Ma Y B, Huang X Y, Chen H, Cao T W, He K, Wang H, Zhang X M, Chen J J. UFLC/MS-IT-TOF guided isolation of anti-HBV active chlorogenic acid analogues from *Artemisia capillaris* as a traditional Chinese herb for the treatment of hepatitis. J Ethnopharmacol. 2014; 156:147-54.

We claim:

1. A composition for treatment of and maintaining the health of the liver, comprising a mixture of enriched plant extracts, wherein the enriched plant extracts comprise *Artemisia capillaris* extract enriched for at least one polymer or biopolymer, an *Aloe* gel powder enriched for at least one chromone, including aloesin, and *Schizandra chinensis* extract enriched for at least one lignan and organic acid, wherein the mixture of *Artemisia capillaris*, *Schizandra chinensis* and *Aloe* leaf gel powder is in a ratio of 8:4:3.

2. The composition of claim 1, wherein the *Artemisia* extract comprises 0.01% to 99.9% of biopolymers with molecular weight higher than 500.

3. The composition of claim 1, wherein the one or more biopolymers are extracted from *Artemisia* plant with water, methanol, ethanol, alcohol, a water-mixed solvent or a combination thereof.

4. The composition of claim 1, wherein the *Aloe* gel powder comprises *Aloe barbadensis*.

5. The composition of claim 1, wherein the at least one chromone composition comprises about 0.01% to about 100% of one or more chromones.

6. The composition of claim 1, wherein the at least one lignan is isolated from a *Schizandra* extract is Schisandrin.

7. The composition of claim 1, wherein the at least one organic acid is isolated from a *Schizandra* extract includes malic acid.

8. The composition of claim 1, wherein the plant extracts are derived from at least one plant part selected from the group consisting of stems, stem barks, trunks, trunk barks, twigs, tubers, roots, root barks, young shoots, seeds, rhizomes, flowers and other reproductive organs, leaves, other aerial parts or a combination thereof.

9. The composition of claim 1, wherein the composition additionally comprises at least one liver protectant.

10. The composition of claim 9, wherein the liver protectant comprises plant powder or plant extract of milk thistle.

11. The composition of claim 9, wherein the liver protectant comprises plant powder or plant extract of milk thistle, *curcuma, bupleurum,* licorice, *salvia, morus, hovenia,* agrimony, *cudrania,* lyceum, *citrus, prunus,* yellow mume, Korea gim, *dandelion, vitis,* grape seed, *rubus, camellia,* green tea, krill oil, yeast, soy bean; isolated and enriched silymarins, flavonoids, phospholipids, thios, pycnogenols, gelatins, soy lecithin, pancreatic enzymes; natural or synthetic N-acetyl-cysteine, taurine, riboflavin, niacin, pyridoxine, folic acid, carotenes, vitamin A, vitamin B2, B6, B16, vitamin C, vitamin E, glutathione, branched-chain amino acids, selenium, copper, zinc, manganese, coenzyme Q10, L-arginine, L-glutamine, phosphatidylcholine or a combination thereof.

12. The composition of claim 1, wherein the composition further comprises a pharmaceutically or nutraceutically acceptable carrier, diluent, or excipient.

13. The composition of claim 1, wherein the composition comprises from about 0.5 weight percent (wt %) to about 90 wt % of active ingredients of the mixture of plant extracts.

14. The composition of claim 13, wherein the composition is formulated as a tablet, hard capsule, soft gel capsule, powder, granule, liquid, tincture, sachet, ready to drink shot, or lozenge.

15. The composition of claim 1, wherein the composition is administered at a dose of 0.01 to 500 mg/kg of body weight of the animal.

16. A medical composition for maintaining liver function, minimizing liver cell damage, promoting healthy liver, neutralizing toxins, diminishing the action of free radicals on the liver, scavenging reactive oxygen species, reducing oxidative stress, preventing the formation of toxic metabolisms, improving liver detoxification capacity and/or function, liver cleansing, restoring liver structure, protecting liver cells from toxins, helping liver's blood flow and circulation, supporting liver function, alleviating liver pain, purging toxic chemicals and organisms, supporting liver's metabolic process, alleviating liver discomfort, alleviating fatty liver, improving liver detoxification capacity, lowering liver enzymes, increasing SOD, increasing GSH, reducing liver cell peroxidation, reducing fatty acid accumulation, improving liver immune function, promoting liver cell regeneration, improving liver renewal function, stimulating bile release, promoting healthy bile flow, liver rejuvenating, wherein the medical composition contains the composition of claim 1 as an effective ingredient.

17. The medical composition of claim 16, wherein the liver disorder or disease is viral hepatitis, alcohol hepatitis, autoimmune hepatitis, alcohol liver disease, fatty liver disease, steatosis, steatohepatitis, non-alcohol fatty liver disease, drug-induced liver disease, cirrhosis, fibrosis, liver failure, drug induced liver failure, metabolic syndrome, hepatocellular carcinoma, cholangiocarcinoma, primary biliary cirrhosis, bile capillaries, Gilbert's syndrome, jaundice, or any combination thereof.

* * * * *